United States Patent
Mansour et al.

(10) Patent No.: US 11,542,559 B2
(45) Date of Patent: Jan. 3, 2023

(54) METHYLATION-BASED BIOMARKERS IN BREAST CANCER SCREENING, DIAGNOSIS, OR PROGNOSIS

(71) Applicant: King Abdullah University of Science and Technology, Thuwal (SA)

(72) Inventors: Hicham Mansour, Thuwal (SA); Roberto Incitti, Thuwal (SA); Vladimir Bajic, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 0 days.

(21) Appl. No.: 17/042,593

(22) PCT Filed: Mar. 26, 2019

(86) PCT No.: PCT/IB2019/052461
§ 371 (c)(1),
(2) Date: Sep. 28, 2020

(87) PCT Pub. No.: WO2019/186404
PCT Pub. Date: Oct. 3, 2019

(65) Prior Publication Data
US 2021/0079482 A1 Mar. 18, 2021

Related U.S. Application Data

(60) Provisional application No. 62/647,952, filed on Mar. 26, 2018.

(51) Int. Cl.
*C12Q 1/6886* (2018.01)

(52) U.S. Cl.
CPC ..... *C12Q 1/6886* (2013.01); *C12Q 2600/154* (2013.01)

(58) Field of Classification Search
None
See application file for complete search history.

(56) References Cited

FOREIGN PATENT DOCUMENTS

WO 2013/186639 12/2013

OTHER PUBLICATIONS

Feng (PNAS 2010 vol. 107 No. 19 pp. 8689-8694) (Year: 2010).*
Beaucage, et al., "Deoxynucleoside Phosphoramidites—a New Class off Key Intermediates for Deoxypolynucleotide Synthesis", *Tetrahedron Letters*, 22(20):1859-1862 (1981).
Chatterjee, et al., "Comparison of alignment software for genome-wide bisulphite sequence data", *Nucleic Acids Res.*, 40(10): e79, 8 pages (2012).
Conner, et al., "Detection of sickle cell BS-globin allele by hybridization with synthetic oligonucleotides", *PNAS*, 80:278-282 (1983).
Eads, et al., "CpG island hypermethlation in human colorectal tumors is not associated with DNA methyltransferase overexpression", *Cancer Res.*, 59(10):2302-2306 (1999).
Frommer, et al., "A genomic sequencing protocol that yields a positive display of 5-methylcytosine residues in individual DNA strands", *PNAS*, 89(5):1827-1831 (1992).
Gonzalgo, et al., "Rapid quantification of methylation differences at specific sites using methylation-sensitive single nucleotide primer extension (Ms—SNuPE)", *Nucleic Acids Res.*, 25(12):2529-2531 (1997).
Landegren, et al., "A ligase-mediated gene detection technique", *Science*, 241(4869):1077-80 (1988a).
Landegren, et al., "DNA diagnostics—molecular techniques and automation", *Science*, 242(4876):229-237 (1988b).
Leygo, et al., "DNA Methylation as a Noninvasive Epigenetic Biomarker for the Detection of Cancer", *Disease Markers*, vol. 2017, 13 pages (2017).
Li, et al., "Sensitive digital quantification of DNA methylation in clinical samples", *Nature Biotechnol.*, 27(9): 858-863 (2009).
Radding, "Homologous Pairing and Strand Exchange in Genetic Recombination", Ann. Rev. Genetics, 16:405-437 (1982).
Ronneberg, et al., "Methyl at ion profiling with a panel of cancer related genes: Association with estrogen receptor, TP53 mutation status and expression subtypes in sporadic breast cancer", *Molecular Oncology*, 5(1):61-76 (2010).
Sadri, et al., "Rapid analysis of DNA methylation using new restriction enzyme sites created by bisulfite modification", *Nucl. Acids Res.*, 24(24):5058-5059 (1996).
Saiki, et al., "A Novel Method for the Detection of Polymorphic Restriction Sites by Cleavage of Oligonucleotide Probes: Application to Sickle-Cell Anemia", *BioTechnology*, 3:1008-1012 (1985).
Tang, et al., "DNA methyl at ion array analysis identifies breast cancer associated IRPTOR/i, iMGRN1/ iand iRASPN/ ihypomethylation in peripheral blood DNA", *Oncotarget*, 7(39): 64191-64202 (2016).
Toyota, et al., "Identification of differentially methylated sequences in colorectal cancer by methylated CpG island amplification", *Cancer Res.*, 59(10):2307-12 (1999).
Visvanathan, et al., "Monitoring of Serum DNA Methylation as an Early Independent Marker of Response and Survival in Metastatic Breast Cancer: TBCRC 005 Prospective Biomarker Study", *J. Clin. Oncol.*, 35(7):751-758 (2016).
Xiong, et al., "COBRA: a sensitive and quantitative DNA methylation assay", *Nucleic Acids Res.*, 25(12):2532-2534 (1997).
International Search Report for corresponding PCT application PCT/IB2019/052461 dated Jul. 29, 2019.

\* cited by examiner

Primary Examiner — Katherine D Salmon
(74) Attorney, Agent, or Firm — Pabst Patent Group LLP

(57) ABSTRACT

Described are epigenetic biomarkers of breast cancer and their use in breast cancer screening and diagnosing, or to provide disease prognosis in a subject. The epigenetic biomarkers include methylatable regions (MRs), which may be at least one segment from nucleic acid sequences represented in Table 1. Described are also methods of detecting the methylation level of MRs in the subject, the methylation score (mSCORE) of the subject, and using these values to evaluate a breast cancer risk in a subject, or diagnose a subject with breast cancer. Also described are methods of determining a risk of recurrence and disease prognosis in a subject undergoing or having undergone a treatment for breast cancer.

10 Claims, No Drawings
Specification includes a Sequence Listing.

METHYLATION-BASED BIOMARKERS IN BREAST CANCER SCREENING, DIAGNOSIS, OR PROGNOSIS

CROSS-REFERENCE TO RELATED APPLICATIONS

This application is a National Phase application under 35 U.S.C. 371 of PCT/IB2019/052461 filed Mar. 26, 2019, which claims the benefit of and priority to U.S. Ser. No. 62/647,952, filed Mar. 26, 2018, all of which are herein incorporated in their entirety by reference.

REFERENCE TO SEQUENCE LISTING

The Sequence Listing submitted Mar. 26, 2019 as a text file named "KAUST_2018-107_PCT.txt," created on Mar. 26, 2019, and having a size of 31,801 bytes is hereby incorporated by reference pursuant to 37 C.F.R. § 1.52(e)(5).

FIELD OF THE INVENTION

The invention is generally directed to biomarkers for screening, diagnosing, and/or evaluating the outcome of treatment in breast cancer.

BACKGROUND OF THE INVENTION

Breast cancer (BC) is the most frequent cancer among women both in developed and developing countries, with an estimated 1.38 million new cancer cases diagnosed in 2008 worldwide (23% of all cancers). Incidence rates vary from 19.3 per 100,000 women in Eastern Africa to 89.7 per 100,000 women in Western Europe. Rates are high (greater than 80 per 100,000) in all developed regions of the world except in Japan. However, rates are relatively low (less than 40 per 100,000) in most of the developing regions. The range of mortality rates is much smaller (approximately 6-19 per 100,000) because of the more favorable survival rate in developed regions. As a result, BC ranks as the fifth cause of death from cancer overall (458,000 deaths in 2008), but it is still the most frequent cause of cancer death in women in both developing (269,000 deaths, 12.7% of total) and developed regions (189,000). In the United States, during 2011, the estimated new BC cases are 229,060 and the estimated deaths amount to 39,920, for both sexes (BC can also occur in men, although rarely) (2).

Many countries have launched national screening programs for BC awareness and follow-up of subjects with high or middle average risk to develop this disease (e.g., family history of BC, women over 50 years of age, etc.). Mammography is still the only tool used for all BC national screening programs; no screening tool has ever been more carefully studied than screening mammography. In the past 50 years, more than 600,000 women have participated in 10 randomized trials, each involving approximately 10 years of follow-up. The outcome of this assessment is mixed: in a study, the U.S. Preventive Services Task Force estimated the reduction in mortality of approximately 15%-23%. They attributed this improvement mainly to the improvements in screening by mammography (4); but opposite conclusions were derived from other studies, for example (5), where the authors state that despite 30 years of increasingly prevalent use of screening mammograms, the expected mortality benefits have failed to materialize in either trial results or public health data. Moreover, in a Norwegian study the high level of mortality reduction published by the U.S. Services Task Force is challenged (6). The study of Kalager et al. provides additional data pointing at a modest benefit of mammography: making use of the opportunity provided by the systematic screening programs in Norway, the investigators singled out other parameters, such as increased breast-cancer awareness and improvements in treatment. They conclude that the benefit of the Norwegian screening program was small: a 10% reduction in breast-cancer mortality among women between the ages of 50 and 69 years. In this study, with a 10-year course of screening mammography for 2500 women of age 50, the estimated benefit for one woman avoiding death from BC were contrasted to the estimated harms of up to 1000 women having at least one "false alarm", about half of whom undergoing biopsy and to 5 to 15 women being misdiagnosed as having BC, and consequently being treated needlessly.

There remains a need for new and improved methods of screening for breast cancer, diagnosing breast cancer, or providing prognosis in breast cancer treatment outcomes.

Therefore, it is the object of the present invention to provide methods for non-invasive screening of individuals for breast cancer and detecting and diagnosing breast cancer, including early stage breast cancer.

It is another object of the present invention to provide methods for non-invasive diagnosis of breast cancer with high specificity and sensitivity.

It is yet another object of the present invention to provide methods for providing prognosis and treatment outcomes in breast cancer.

SUMMARY OF THE INVENTION

Described are compositions containing epigenetic biomarkers of breast cancer and methods of use thereof in breast cancer screening and diagnosing, or in determining a risk of recurrence and disease prognosis in a subject. The methods allow diagnosis of BC in a subject with a specificity of at least 90% and up to 100% and a sensitivity of at least 90%, more preferably, with a sensitivity of at least 94%, for example 94%, 95%, 96% etc., up to, 100%.

The epigenetic biomarkers include methylatable regions (MRs) of DNA isolated from a subject. The MR include the sequences shown in Table 1, segments thereof, or variants thereof. The epigenetic biomarker may be any segment of the one or more SEQ ID NOS:1-219, the one or more SEQ ID NOS:1-219, or the one or more SEQ ID NOS: 1-219 and their 5' and/or 3' flanking regions. In some aspects, the one or more MRs may have a length of about 50 nucleotides (nt), such as between 45 nt and 55 nt. The one or more MRs may be the one or more SEQ ID NOS:1-219. The one or more MRs may be the one or more SEQ ID NOS:1-219 with 5' and/or 3' flanking sequence(s), such as a flanking sequence extending up to but not including a first encountered methylated residue.

Methods for diagnosing the presence, absence, or risk of breast cancer (BC) in an individual, and methods for prognosing the outcome of a breast cancer treatment or risk of recurrence in an individual are provided. The methods include the steps of (i) assaying genomic nucleic acids from the subject for the methylation level in the methylatable regions (MRs) of genomic DNA comprising SEQ IDs NOs: 1 to 219; and diagnosing the presence/absence of BC or risk of developing BC or prognosis of the BC, based on Equation 1:

$$mSCORE = COV \times mTOT \qquad \text{Equation (1).}$$

where COV is the number of MRs for the patient, which contain at least one methylated residue, and mTOT, is the sum of methylated residues of all considered MRs for the patient In other aspects, the method further includes determining the methylation score (mSCORE) of the subject. Thus, the disclosed methods generally includes obtaining the total methylation (mTOT) for the subject, the mTOT represented by the sum of the methylation levels of all 219 MRs considered for the subject; obtaining coverage (COV) for the subject, the COV represented by the number of MRs for the subject containing at least one methylated residue; and calculating the mSCORE from Equation (1):

The individual is diagnosed as not having breast cancer if the methylation score defined by equation (1) across all 219 MRs is zero (mSCORE)=0).

The individual is diagnosed as potentially having breast cancer if the methylation score defined by equation (1) across all 219 MRs is greater than 0 with increasing probability of having cancer as the score increases. The individual is diagnosed as having/not having cancer with a specificity of at least 90% and up to 100% and a sensitivity of at least 90%, more preferably, with a sensitivity of at least 94%, for example 94%, 95%, 96% etc., up to, 100%, using the below values of mSCORE as a decision threshold.

| mSCORE threshold | Sensitivity |
|---|---|
| mSCORE > 23 | Sensitivity = 100% |
| mSCORE > 34 | Sensitivity = 98% |
| mSCORE > 49 | Sensitivity = 96% |
| mSCORE > 199 | Sensitivity = 94% |
| mSCORE > 239 | Sensitivity = 92% |
| mSCORE > 274 | Sensitivity = 90% |
| mSCORE > 311 | Sensitivity = 88% |
| mSCORE > 329 | Sensitivity = 86% |
| mSCORE > 419 | Sensitivity = 84% |
| mSCORE > 447 | Sensitivity = 82% |
| mSCORE > 495 | Sensitivity = 80% |
| mSCORE > 503 | Sensitivity = 78% |
| mSCORE > 531 | Sensitivity = 76% |
| mSCORE > 702 | Sensitivity = 74% |
| mSCORE > 809 | Sensitivity = 72% |
| mSCORE > 923 | Sensitivity = 70% |
| mSCORE > 930 | Sensitivity = 68% |
| mSCORE > 1099 | Sensitivity = 66% |
| mSCORE > 1126 | Sensitivity = 64% |
| mSCORE > 1319 | Sensitivity = 62% |
| mSCORE > 1367 | Sensitivity = 60% |
| mSCORE > 1507 | Sensitivity = 58% |
| mSCORE > 2885 | Sensitivity = 56% |
| mSCORE > 3101 | Sensitivity = 54% |
| mSCORE > 3242 | Sensitivity = 52% |
| mSCORE > 3599 | Sensitivity = 50% |
| mSCORE > 3688 | Sensitivity = 48% |
| mSCORE > 3814 | Sensitivity = 46% |
| mSCORE > 4170 | Sensitivity = 44% |
| mSCORE > 4399 | Sensitivity = 42% |
| mSCORE > 5001 | Sensitivity = 40% |
| mSCORE > 5084 | Sensitivity = 38% |
| mSCORE > 5199 | Sensitivity = 36% |
| mSCORE > 5235 | Sensitivity = 34% |
| mSCORE > 5249 | Sensitivity = 32% |
| mSCORE > 5611 | Sensitivity = 30% |
| mSCORE > 5887 | Sensitivity = 28% |
| mSCORE > 6335 | Sensitivity = 26% |
| mSCORE > 6967 | Sensitivity = 24% |
| mSCORE > 7425 | Sensitivity = 22% |
| mSCORE > 13577 | Sensitivity = 20% |
| mSCORE > 16553 | Sensitivity = 18% |
| mSCORE > 17099 | Sensitivity = 16% |
| mSCORE > 17167 | Sensitivity = 14% |
| mSCORE > 19447 | Sensitivity = 12% |
| mSCORE > 20367 | Sensitivity = 10% |
| mSCORE > 21227 | Sensitivity = 8% |
| mSCORE > 24562 | Sensitivity = 6% |
| mSCORE > 37208 | Sensitivity = 4% |
| mSCORE > 39341 | Sensitivity = 2% |

The Table above provides the decision threshold (by which cancer is diagnosed). If the decision threshold is too high, one might wrongly diagnose as normal a patient that have cancer (False Negatives). For each of the mSCORE values in the table above allows a determination of the Specificity (which is always 100%) and the Sensitivity that one can get by using that score as a deciding threshold for screening.

As an illustration, an individual might be screened as:

1/ Not having breast cancer if the methylation score defined by equation (1) across all 219 MRs is zero (0), 2/ Having a lower risk of having breast cancer or potential to develop breast cancer if the methylation score defined by equation (1) across all 219 MRs is greater than zero but less than or equal to 199 i.e., mSCORE>0 and ≤199.

3/ Having a medium risk of having breast cancer or potential to develop breast cancer if the methylation score defined by equation (1) across all 219 MRs is greater than 199 but less than or equal to 495 i.e., mSCORE>199 and ≤495.

4/ Having a higher risk of having breast cancer or potential to develop breast cancer if the methylation score defined by equation (1) across all 219 MRs is greater than 495 but less than or equal to 1099 i.e., mSCORE>495 and ≤1099, 5/ Having a very high risk of having breast cancer or potential to develop breast cancer if the methylation score defined by equation (1) across all 219 MRs is greater than 1099 i.e., mSCORE>1099.

The disclosed methods further include administering to the subject anti-cancer treatment when the subject is diagnosed as having breast cancer. In some embodiments, the methods might also include further conclusive detection for the presence of breast cancer. Conclusive detection is preferably done by histopathology. Techniques such as fine needle aspiration (FNA) and a core biopsy are required for the extraction of suspected tumor tissue and subsequent histological evaluation. For example, mSCORE numbers that deviate from the selected threshold providing 90% sensitivity can result in the patient being referred to a further confirmatory test.

The observation that mSCORE increases or decreases after treatment might also be an indication of progression/regression of the disease. Thus, the method steps disclosed herein can, in some embodiments, be conducted before and after cancer treatment has commenced, for prognosis the outcome of cancer treatment. In these embodiments, the method includes (i) assaying genomic nucleic acids from the subject for the methylation level in the methylatable regions (MRs) of genomic DNA comprising SEQ IDs NOs: 1 to 219 before initiation of cancer treatment; (ii) assaying genomic nucleic acids from the subject for the methylation level in the methylatable regions (MRs) of genomic DNA comprising SEQ IDs NOs: 1 to 219 during cancer treatment or after completion of cancer treatment.

If the mSCORE defined in equation (1) calculated across all 219 MRs increases, the individual has a higher chance of breast cancer recurrence and negative prognosis for the positive outcome of the treatment. If the score defined in equation (1) calculated across all 219 MRs decreases, the individual has a lower risk of breast cancer recurrence and increased chances of positive effect of the therapy. For example, a 10% or more increase in in mSCORE following treatment is indicative of a higher change of breast cancer recurrence. Conversely, a 10% or more decrease in mScore following treatment is indicative of reduced risk of breast cancer recurrence. For example, if a subject's mSCORE before commencement of cancer therapy is 35, and the mSCORE after therapy increases to 500 the therapy was not successful and the individual has a higher risk of breast cancer recurrence.

In another embodiment, response to treatment for BC, the prognosis of BC, or a combination thereof, can be determined by monitoring a change in methylation of specific MRs from the 219 MR shown in Table 1. For example, if some of the MRs of a subject's DNA are found to be methylated before treatment and are found to be un-methylated after treatment the response to treatment may be considered favorable and the prognosis is favorable (positive prognosis for positive outcome).

Methods of detecting DNA methylation level of an epigenetic biomarker in a subject generally include analyzing isolated DNA from a sample of the subject for DNA methylation, to determine the number of MRs for the patient, which contain at least one methylated residue, and the sum of methylated residues of all considered MRs for the patient. The sample can be tissue, blood, spittle, serum, plasma, urine, sputum, biopsy, or stool.

Analyzing the subject's isolated DNA for DNA methylation may include subjecting the isolated DNA to methylation quantification assays, such as Combined Bisulfite Restriction Analysis (COBRA), MethyLight, methylation-sensitive single-nucleotide primer extension (Ms-SNuPE), methylated CpG island amplification (MCA), Methyl-BEAMing, and methylation-specific polymerase chain reaction (MSP).

Generally, detecting the methylation level includes detecting methylation of at least one nucleotide residue in the epigenetic biomarker. The methylation level may be detected by absolute quantification, such as by detecting the number of methylated nucleotide residue(s) in the epigenetic biomarker, the position of methylated nucleotide residue(s) in the epigenetic biomarker, both the number and the position of methylated nucleotide residue(s) in the epigenetic biomarker.

The subject may undergo one or more additional diagnostic assay(s). Exemplary additional diagnostic assay(s) include blood tests, non-invasive imaging, tissue biopsy, Her2 testing, hormone status testing, and combinations thereof.

The subject may also undergo an anti-cancer treatment. Exemplary anti-cancer treatments include surgery, chemotherapy, radiation therapy, immunotherapy, gene therapy, or combinations thereof. For example, chemotherapy may include a treatment with an effective amount of an anti-cancer agent. Exemplary anti-cancer agents include anthracyclines doxorubicin (Adriamycin®), pegylated liposomal doxorubicin (Doxil®), and epirubicin (Ellence®); taxanes paclitaxel (Taxol®) and docetaxel (Taxotere®); 5-fluorouracil (5-FU); cyclophosphamide (Cytoxan®); carboplatin (Paraplatin®); albumin-bound paclitaxel (Abraxane®); platinum agents (cisplatin, carboplatin); vinorelbine (Navelbine®); capecitabine (Xeloda®); gemcitabine (Gemzar®); ixabepilone (Ixempra®); eribulin (Halaven®), trastuzumab (Herceptin®), and combinations thereof.

Generally, the subject is a mammal, such as a domestic animal, farm animal, laboratory animals, non-human primate, or a human. The subject may be a human aged 50 years or older. The subject may or may not have a prior history of cancer. In some aspects, the subject may have a personal history of breast cancer, including surgery for breast cancer; a family history of breast cancer; have breast cancer; and/or be positive for one or more breast cancer genetic biomarkers BRCA, ATM, P53, HER2, AR, CHEK2, PTEN, CDH1, STK11, PALB2, and combinations thereof.

The subject may be asymptomatic for breast cancer. In some aspects, the subject may have one or more symptoms of breast cancer. Exemplary symptoms include fibrosis and/or simple cysts, mild hyperplasia, adenosis (non-sclerosing), phyllodes tumor (benign), single papilloma, fat necrosis, duct ectasia, periductal fibrosis, squamous and apocrine metaplasia, epithelial-related calcifications, other tumors (lipoma, hamartoma, hemangioma, neurofibroma, adenomyoepithelioma), mastitis usual ductal hyperplasia (without atypia), fibroadenoma, sclerosing adenosis, several papillomas (called papillomatosis), radial scar, atypical ductal hyperplasia (ADH), atypical lobular hyperplasia (ALH), and combinations thereof.

The sample obtained from the subject may be tissue, cells, and/or a bodily fluid. For example, the sample may be cells, tissue, serum, plasma, urine, spittle, sputum, and stool. The sample may be obtained via non-invasive or minimally invasive procedures.

Also described is a substrate, such as a chip or a microchip, containing one or more nucleic acid sequences attached thereto.

Also described are kits containing the substrate and/or materials for analyzing the isolated DNA for methylation.

DETAILED DESCRIPTION OF THE INVENTION

I. Definitions

As used herein, the term "detect", "detecting", "determine" or "determining" generally refers to obtaining information. Detecting or determining can utilize any of a variety of techniques available to those skilled in the art, including for example specific techniques explicitly referred to herein. Detecting or determining may involve manipulation of a physical sample, consideration and/or manipulation of data or information, for example utilizing a computer or other processing unit adapted to perform a relevant analysis, and/or receiving relevant information and/or materials from a source. Detecting or determining may also mean comparing an obtained value to a known value, such as a known test value, a known control value, or a threshold value. Detecting or determining may also mean forming a conclusion based on the difference between the obtained value and the known value.

As used herein, the term "biomarker" or "marker" refers to a substance, molecule, or compound that is produced by, synthesized, secreted, or derived, at least in part, from the cells of the subject and is used to determine presence or absence of a disease, and/or the severity of the disease.

The term "isolated", as used herein, refers to an agent or entity that has either (i) been separated from at least some of the components with which it was associated when initially produced (whether in nature or in an experimental setting); or (ii) produced by the hand of man. Isolated agents or entities may be separated from at least about 10%, at least about 20%, at least about 30%, at least about 40%, at least about 50%, at least about 60%, at least about 70%, at least about 80%, at least about 90%, or more of the other components with which they were initially associated. In some embodiments, isolated agents are more than 90%, 91%, 92%, 93%, 94%, 95%, 96%, 97%, 98%, or 99% pure.

As used herein, the term "nucleic acid molecule" is used broadly to mean any polymer of two or more nucleotides, which are linked by a covalent bond such as a phosphodiester bond, a thioester bond, or any of various other bonds known in the art as useful and effective for linking nucleotides. Such nucleic acid molecules can be linear, circular or supercoiled, and can be single stranded or double stranded, e.g. single stranded or double stranded DNA, RNA or DNA/RNA hybrid. In some embodiments, nucleic acid molecules are or include nucleic acid analogs that are less susceptible to degradation by nucleases than are DNA and/or RNA.

The term "Methylatable Region", denoted here as MR, is a DNA region of about 50 nucleotides (nt) in length, such as between 45 nt and 55 nt in length. Exemplary MR length include 45 nt, 46 nt, 47 nt, 48 nt, 49 nt, 50 nt, 51 nt, 52 nt, 53 nt, 54 nt, and 55 nt.

The term "methylation level" of an MR refers to the number of methylated residues in an MR, the position of the methylated residues in an MR, or both. Methylation level of an MR may be represented by 0 nt being methylated, or 1, 2, 3, 4, 5, 6, 7, 8, 9, 10, etc. nt residues being methylated in the same MR.

The term "total methylation" of a subject, denoted here as mTOT, is the sum of methylated residues of all considered MRs for the subject.

The term "coverage" of a subject, denoted here as COV, is the number of MRs for the subject, which contain at least one methylated residue.

The term "methylation score", denoted here as mSCORE, for a subject is defined as a product of the patient's coverage and total methylation of 219 MRs, i.e., as:

$$mSCORE = COV \times mTOT \quad \text{Equation (1)}.$$

As used herein, the term "sensitivity" refers to the ability of a test to correctly identify true positives, i.e., patients with BC. For example, sensitivity can be expressed as a percentage, the proportion of actual positives which are correctly identified as such (e.g., the percentage of test subjects having BC correctly identified by the test as having BC). A test with high sensitivity has a low rate of false negatives, i.e., the cases of BC not identified as such. Generally, the disclosed methods have a sensitivity of at least 90%, at least 92%, at least 92%, at least 93%, at least 94%, at least 95%, at least 96%, at least 97%, at least 98%, at least 99%, or 100%.

As used herein, the term "specificity" refers to the ability of a test to correctly identify true negatives, i.e., the individuals that have no BC. For example, specificity can be expressed as a percentage, the proportion of actual negatives which are correctly identified as such (e.g., the percentage of test subjects not having BC correctly identified by the test as not having BC). A test with high specificity has a low rate of false positives, i.e., the cases of individuals not having BC but suggested by the test as having BC. Generally, the disclosed methods have a specificity of at least 90%, at least 92%, at least 94%, at least 95%, at least 96%, at least 97%, at least 98%, at least 99%, or 100%.

As used herein, the term "sample" refers to body fluids, body smears, cell, tissue, organ or portion thereof that is isolated from a subject. A sample may be a single cell or a plurality of cells. A sample may be a specimen obtained by biopsy (e.g., surgical biopsy). A sample may be cells from a subject that are or have been placed in or adapted to tissue culture. A sample may be an intact organ or tissue. The sample may include circulating tumor cells or free tumor DNA. A sample may be one or more of cells, tissue, serum, plasma, urine, spittle, sputum, and stool.

As used herein, the terms "tissue", in a context of a sample, refers to a tissue in or from a body. The tissue may be from an organ with a pathology, for example, tissue containing tumors, whether primary or metastatic lesions. In some embodiments, an organ or tissue is normal (e.g., healthy). The term "control tissue" is used to mean an organ or tissue other than the organ or tissue of the test subject.

As used herein, the terms "subject," "individual" or "patient" refer to a human or a non-human mammal A subject may be a non-human primate, domestic animal, farm animal, or a laboratory animal. For example, the subject may be a dog, cat, goat, horse, pig, mouse, rabbit, or the like. The subject may be a human. The subject may be healthy or suffering from or susceptible to a disease, disorder or condition. A patient refers to a subject afflicted with a disease or disorder. The term "patient" includes human and veterinary subjects. A "control" sample or value refers to a sample that serves as a reference, usually a known reference, for comparison to a test sample. For example, a test sample can be taken from a test subject, and a control sample can be taken from a control subject, such as from a known normal (non-disease) individual or a known and diagnosed individual. A control can also represent an average value gathered from a population of similar individuals, e.g., disease patients or healthy individuals with a similar medical background, same age, weight, etc. A control value can also be obtained from the same individual, e.g., from an earlier-obtained sample, prior to disease, or prior to treatment. One of skill will recognize that controls can be designed for assessment of any number of parameters.

As used herein, the term "screening" refers to testing a sample from an individual, or from a population of individuals, with known or unknown risk of developing a disease, and determining which individuals have to undergo more in-depth diagnostic investigation.

As used herein, the term "diagnosing" refers to steps taken to identify the nature of a disease or condition that a subject may be suffering from. As used herein, the term "diagnosis" refers to the determination and/or conclusion that a subject suffers from a particular disease or condition. The term "diagnosing" may denote the disease's identification (e.g., by an authorized physician or a test approved from a health care authority).

As used herein, the term "prognosis" relates to a prediction of a disease course, disease duration, and/or expected survival time. Prognosis informs of the likely outcome or course of a disease; the chance of recovery or recurrence. A complete prognosis may include the expected duration, the function, and a description of the course of the disease, such as progressive decline, intermittent crisis, or sudden, unpredictable crisis, as well as duration of the disease, or mean/median expected survival. Typically, scientifically-deduced prognosis is based on information gathered from various epidemiologic, pathologic, and/or molecular biologic studies involving subjects suffering from a disease for which a prognosis is sought. The term "prognosis" may denote the forecasting of disease evolution.

For example, prognosis may include estimating cancer-specific survival (the percentage of patients with a specific type and stage of cancer who have not died from their cancer during a certain period of time after diagnosis), relative survival (the percentage of cancer patients who have survived for a certain period of time after diagnosis compared to people who do not have cancer), overall survival (the percentage of people with a specific type and stage of cancer who have not died from any cause during a certain period of time after diagnosis), or disease-free survival (also referred to as recurrence-free or progression-free survival, is the percentage of patients who have no signs of cancer during a certain period of time after treatment). Prognosis may also include a negative prognosis for positive outcome, or a positive prognosis for a positive outcome.

As used herein, "good prognosis" or "positive prognosis" indicates that the subject is expected (e.g. predicted) to survive and/or have no, or is at low risk of having, recurrence or distant metastases within a set time period. The term "low" is a relative term. A "low" risk can be considered as a risk lower than the average risk for an heterogeneous cancer patient population. A "low" risk of recurrence may be considered to be lower than 5%, 10%, or 15% the average risk for an heterogeneous cancer patient population. The risk will also vary in function of the time period. The time period can be, for example, five years, ten years, fifteen years or even twenty years after initial diagnosis of cancer or after the prognosis was made.

As used herein, "poor prognosis" or "negative prognosis" indicates that the subject is expected e.g. predicted to not survive and/or to have, or is at high risk of having, recurrence or distant metastases within a set time period. The term "high" is a relative term. A "high" risk can be considered as a risk higher than the average risk for a heterogeneous cancer patient population. A "high" risk of recurrence may be considered to be higher than 5%, 10%, or 15% the average risk for an heterogeneous cancer patient population. The risk will also vary in function of the time period. The time period can be, for example, five years, ten years, fifteen years or even twenty years of initial diagnosis of cancer or after the prognosis was made.

As used herein, the terms "treatment" and "treating" refer to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. It is understood that treatment, while intended to cure, ameliorate, stabilize, or prevent a disease, pathological condition, or disorder, need not actually result in the cure, amelioration, stabilization or prevention.

As used herein, the term "effective amount" refers to a sufficient amount of the compound to provide the desired result. The exact amount required will vary from subject to subject, depending on the species, age, and general condition of the subject, the severity of the disease that is being treated, the particular compound used, its mode of administration, and the like. Thus, it is not possible to specify an exact "effective amount." However, an appropriate effective amount can be determined by one of ordinary skill in the art using only routine experimentation.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%.

II. Compositions

The methylation of certain regions of genomic DNA has been discovered be useful in determining the presence or a high likelihood of developing BC and can therefore serve as epigenetic markers of BC and/or determining the outcome of BC therapy. Accordingly, compositions containing these epigenetic biomarkers of breast cancer are useful in detecting the presence of breast cancer in a subject, the likelihood of developing cancer or determining the outcome of breast cancer treatment (prognosis). The compositions include methylatable regions (MRs) of DNA isolated from a subject, or variants thereof.

A. Methylatable Regions

The epigenetic biomarkers include methylatable regions (MRs), which may be any segment of the one or more SEQ ID NOS:1-219 presented in Table 1. The MRs may be the one or more SEQ ID NOS:1-219. The MRs may be the one or more SEQ ID NOS: 1-219 and their 5' and/or 3' flanking regions.

TABLE 1

Chromosome (Chr), location, and sequences of SEQ ID NOS: 1-219.

| Chr | Location | Sequence | SEQ ID NO: |
|---|---|---|---|
| 2 | 202047353 | ctaaaaatacaaaaaattagccgggcgtggtggcgcatgcttgtaatccca | 1 |
| X | 118603112 | cgccgcgtctccgcctgcctccctgcgccgcgcgctctccagtgccggctc | 2 |
| X | 11776527 | ccgggaccggggcggggcggggcggacggccgcgcggagctgagggac | 3 |
| 1 | 18958199 | ggcctcgccgcgactccgccgcccggaactcggggtccttggagaggctgc | 4 |
| X | 149533500 | tggtttcgagccgctcgggacaggagggcaagtgtaggcgatgggggaggg | 5 |
| 11 | 118481804 | cgtccctcgcgtagcgccactcagccgccggggccagagcgggagtcaagg | 6 |
| X | 150152081 | acgcgttccccgagctccccgctttcgggggtcggcccctcggcggacgc | 7 |
| 4 | 166796009 | tcgcgcgcgcggggcggcgcttccctctcgccgcctaaggtcggaggcgca | 8 |
| 5 | 60241058 | agcgctggaaactgggtggacggcatgggttggtctcaggatttgttccgc | 9 |
| 11 | 31840688 | gtccctgcgcgccttgatccgggcggcggctaagggagagccgagcacaga | 10 |
| 11 | 75480106 | agcgctctcacggaggacctgcgctgtcgcgcgagggggtctgggagatggg | 11 |
| 9 | 970863 | cggctgggttcgcgccgccgccccgggggcccttggctcaaatttcacctcg | 12 |
| 11 | 636692 | agaggctgcggggggggggcggcgggatgagctaggcgtcggcggttgagt | 13 |
| X | 153657177 | tggtgctgtggtcgagtgaccggtgagcgggccggggtgggatgcgctgtg | 14 |
| 7 | 27196396 | caaatatgcggccaaagaatccgcccgcgcccggcgggcctggcgcgtccc | 15 |

TABLE 1-continued

Chromosome (Chr), location, and sequences of SEQ ID NOS: 1-219.

| Chr | Location | Sequence | SEQ ID NO: |
|---|---|---|---|
| 7 | 27204896 | cgccttggactggaagctgcacgggctgaagtcggggtgctcggccagcgt | 16 |
| 7 | 27204946 | tcgccgcctgccggggaggctggcccagggtccccggcgcatagcggccaa | 17 |
| 7 | 27204996 | acgctcagctcatccgcggcgtcggcgcccagcaggaacgagtccacgtag | 18 |
| 7 | 27205096 | ccgcccggcccgacccacggaaattatgaaactgcagattttcatgtaacaa | 19 |
| 2 | 234388960 | gaataggacaaaaggcagatttaggagagacccagagtccgtgagtcgggg | 20 |
| 22 | 24181081 | caccgcggcggtggtgaggacacaggctgcggtgtaagcccgcgtcaccgc | 21 |
| X | 49054159 | gggtgggagcacacctgaaggggtactcgaactcgacctcgatgctgaggt | 22 |
| X | 129244649 | tcgccgccaatggcaagttggagggagagatgcaaataccaggtgagac | 23 |
| X | 129474136 | tgaaccctgcttcctcgaccccctgggaggccgccttcttcaggcgcctc | 24 |
| 13 | 49795323 | cggccgcctcggggcgggagagaggccaccggcagaccgtccgcgtcctgc | 25 |
| 15 | 41165529 | tcggcctgggtgcccaccagcagcacaggcgcctgggggttgtgcgtgcgg | 26 |
| 19 | 7544386 | ccctgggcgccggacccaggcatctccatttagcaacctcctggctgatgc | 27 |
| 19 | 2252615 | cttgggtccccggtctgcgagggtcacacggtcctcccggacggcctctcc | 28 |
| 19 | 46285548 | cccaggaagcccgggtccaacaccagctgctggagccgcctcagccgcacc | 29 |
| 7 | 30516171 | agggagcaacgtgcgtgtgtgtgcacatacactaattctgagacactgtgc | 30 |
| 10 | 103538925 | tccaatccacaccccgccggagaccgcagctcgctccgacgcgcgcttcctg | 31 |
| 10 | 103538975 | gcgccgggcgttcaaagcgccgcggactcactgccgaccgttcaaatgcaa | 32 |
| 10 | 103538929 | atccacaccccgccggagaccgcagctcgctccgacgcgcgcttcctgcgcc | 33 |
| 17 | 42287859 | cgtcagccttccacccacccccaggggcgcgcgctcccccgcgcagcagcc | 34 |
| 17 | 44896583 | tccgcccgctctctggcctctcgtcctggccgcgggaggtcacttcccggg | 35 |
| 17 | 76164088 | tgggattacaggtgtgagccaccgctcccggccttgcacaccatcttaagt | 36 |
| 4 | 41748264 | cttggccgcggccgctgcggctgccgctgcgcgctcctgcttgcgaaactt | 37 |
| 4 | 41754914 | gaggctgttttaccgcaggcgaagcacaataacatgggaatgaataaaata | 38 |
| 4 | 13543872 | tgcgtctcggtgagcttcagcgacgcggccaggtctgcgcgctcgggcccg | 39 |
| 12 | 109023884 | ctccgacagaggcgtctccagtgaccacgtcctatttgtctcaacacttgc | 40 |
| 12 | 7024225 | tctcctgctcttcccacggcgcccctctccgttcgcgcttcctccccctct | 41 |
| 6 | 150285892 | gatgcccccgaacatcgcgttctaccccaacatcgcgatccctccgaacat | 42 |
| 6 | 82461106 | catcaagtaaactgaaacactcaacaccgtccacgcacgtcagtttactgg | 43 |
| 3 | 141496389 | ggatggtctcgatctcctgacctcgtgatccgcccggagatggccctctt | 44 |
| 1 | 53386650 | gacccgcgaactttgccccccaccccctcgtccccgctccatactatccttg | 45 |
| 1 | 12039537 | gccctcctaaaatgctggaattacaggcttgagccaccgcgcccggtcgat | 46 |
| 2 | 200327191 | gacggttcgcccagggtgggcttcagccctttcccagagtgctccgggcgt | 47 |
| 2 | 106681899 | ctgcgggcagcgctggccacgcggcccccgccgccggccgggttctccgtgg | 48 |
| 14 | 77492887 | ttcgtagtccatgccgggcttggagacggcgtcgaaggcgaaaacgcggcc | 49 |
| 2 | 27887695 | aggcccaggcgggaggatcgctttagcccaggagtttgagaggaggctggg | 50 |
| 7 | 27196385 | ggcaagaggctcaaatatgcggccaaagaatccgcccgcgcccggcgggcc | 51 |
| 7 | 27204935 | ctcggccagcgtcgccgcctgccggggaggctggcccagggtccccaggcc | 52 |
| 7 | 27205085 | cagcgcctggcccgcccggcccgacccacggaaattatgaaactgcagatt | 53 |
| 7 | 27205185 | gttgccggcgcccgcgcccccattggccgtgcgcgtcacgtgcccgtccag | 54 |
| 12 | 54355267 | tcccgcgcccgacagcgccggcagctctggtctcctccggagggctgctgt | 55 |
| 13 | 95363685 | gtggaaggcgccgcgccgcgcggtcgggtagcccggcggcggttctccgtg* | 56 |
| X | 118826424 | gcgccgccgccgcccgcccgggaagacacgagcgcgcgcgcgtgcacacat | 57 |
| 9 | 135462421 | agagcgccgagcgcggcgcagggactggagttctcgccagcttcgggttct | 58 |
| 20 | 21502048 | ccggcgccgggcgcggcccaggcgacactcgcctcccaaactccagtcttc | 59 |
| 14 | 99736297 | cgcgcagcgaagaagccgcccgcgggctgcgggctggccaggtcgggagcgccgca | 60 |
| 16 | 2029710 | ctgcccgcggtgcttctggccagtcttgccacacggtcaagccgcagtgg | 61 |
| 16 | 857315 | taccttttcaaaatgtcacctctccccgcggtgtgaccctcgaaagctaga | 62 |
| 7 | 100965651 | tatcactgtggcatgatatcactgtggccgtccacctgggagccgatttat | 63 |
| 11 | 17743714 | ggatccggaggaaaatccgcaaactgggccagctgtccctcagcgacgcct | 64 |
| 11 | 2907649 | tggtgtccctcgagggctccgcgcggcctgagccctcacacacctgctgg | 65 |
| 17 | 7111617 | ccgcccctggccgccgcctcttcccccagccagtcagtgcggaaggccctg | 66 |
| 22 | 37583925 | tttggggagggagcggcagggcaacttttctcggtccaggcaggccgtgca | 67 |
| 15 | 37390339 | cgtacatggaagcgggaaccccctactccgtccatcccgccgtaatgggca | 68 |
| 15 | 37395089 | ggtgggagggggaaaaaaacaaaaacgctgcgggcgttttcgactttga | 69 |
| 2 | 73147553 | cttttcgaaccctgtagcgctgttgctcgcggtccatcgtcgccgctgca | 70 |
| 7 | 23510904 | gcgacacctcctccgcctccgcctgcgctcgcggtggctctcggcttcgcg | 71 |
| 7 | 2681434 | acgctccccgcagacagctgggctcaggcctggcgcgttgggtgccggggc | 72 |
| 8 | 63999226 | atgactagcgcgtaccctgacccccttccgcaccaatatttatatatttat | 73 |
| 1 | 78512035 | caggctctcccgcctctccgccgcgccgccgccgcgcgtatttctgt | 74 |
| 4 | 134072669 | aacgcgccgcgtttcagccagccggtctacgacgtgtatgtgactgaaaac | 75 |
| 4 | 113559200 | cagcactttggggaggccgacgcgggaggatcacttgaggtcaggagttcga | 76 |
| 15 | 81291994 | tatgccgataaattgaaacgtcatcctagttaaaagtaacgttttttaact | 77 |
| 16 | 31488355 | ggagggggcgggtcaagggtacagggctgtggggcggggccttggagggcg | 78 |
| 18 | 59992119 | gcatccactttcggaaggccgggcctcgaagggtgggcgcgggggcagga | 79 |
| 1 | 2980431 | cgcgagccgcaggacgcgggcgctgtgggtaacgaagttgctcccggtgtg | 80 |
| 1 | 2980531 | cacggctgcgggcgcgtgaacacacggctgaaggtcataggcagcgcat | 81 |
| 1 | 2980631 | gggaaagcgtgtgaaaccgattccgtttattgccccagcggcggggagc | 82 |
| 1 | 91191727 | ccgcgtcccgggctgcgctaggcattccagcactgggccgcgcgtgatt | 83 |
| 1 | 147231206 | tcccccaggaagactcagcagctgtgcccagcacgagcatacggaatatg | 84 |
| 1 | 150603136 | ttacaggcctgctgggcgcggtgactcacgcctgtaatgccagcactctg | 85 |
| 1 | 153652296 | aaggcggaggtgagacgtggcacaccccgtcccgccgcttagccgcaggg | 86 |
| 2 | 66654014 | ctgcagaacaccgccgggacccggcacccggacgcgcaagggcgacagggc | 87 |
| 5 | 175223762 | gcggaggagctgcagcctccaacaggttcgtagaacgcgcgctcgctccct | 88 |
| 2 | 133428403 | ttaactgtctcacttgcccgggccgccctcccttctcccgcctgcgcgcac | 89 |
| 4 | 139936042 | aacggctcgcagctatccaccgaattaagcctactataatccccttccttc | 90 |

TABLE 1-continued

Chromosome (Chr), location, and sequences of SEQ ID NOS: 1-219.

| Chr | Location | Sequence | SEQ ID NO: |
|---|---|---|---|
| 4 | 147569244 | taatcacgtctatttaaattctagcgcggtccgccgcgctctcaccgggaa | 91 |
| 2 | 202900259 | tcatggtggccgtggcgcacgtggccggcttcctctagaggaccgcgccg | 92 |
| 3 | 12200501 | acccgcggaggcaggacccgaggctcttccgacctgcatactcagtaagat | 93 |
| 1 | 2461902 | ggcacaatgtccgggctgtgggaacgcgctcgccctcattagcatcccggg | 94 |
| X | 119694683 | ggctgacaccaggagtgagcagaacgaggggggagagcgaatgaggaggca | 95 |
| 21 | 46352874 | aggacggggccggggccggagagggcgggggagggcgctcctgggaggtca | 96 |
| 8 | 145700715 | actaccgggctcaggggcgcgcggtgccggcccctgctgtccccgaagaag | 97 |
| 1 | 1109282 | cccaggaccttgtgggctgggcaggtaagaagcgccggcggccaccagctg | 98 |
| 4 | 4860242 | tattattattattattaacagcaaacattaaatcacgttttctccgaa | 99 |
| 2 | 233252393 | cagggaccaggagggctcggcggggccaccacccccgcgtgcacagtggag | 100 |
| 3 | 9989155 | cggtggcggcagccccgcgcccaggccgagcagagtcagggctgccagcgc | 101 |
| 3 | 9989255 | acgcccagccgcgcctgcgagccgtaaggagtcggtaagcatgtaggcggat | 102 |
| 3 | 9989305 | tcgcagcgccgaagccacgagcaccagcaccgcggccaccaatgccagccg | 103 |
| 2 | 27887687 | actttggagggcccaggcggaggatcgctttagcccaggagtttgagagg | 104 |
| 4 | 4228188 | cgcgcagccagccggcaccccgtgcgtgtccttgaggcggaagaggcggc | 105 |
| 5 | 60241105 | ccgcgccttgtggagatcgctgtcaagggaagtgaaggagcacgtgggcac | 106 |
| 7 | 20827096 | gggcgcttgtgttgtgtgcgcgcaccaaagctggtagtggggaatgggaac | 107 |
| 7 | 20830796 | ataaagcgtgaagagggatcgctgggtagctgagcgccgccggcggccgcc | 108 |
| 7 | 155259773 | gccgcgcgctgggaggttaatagcgactgacgacaaagggccaaggtgcaa | 109 |
| 8 | 90913486 | tggtctggaacttctgacctcaggtgatccgtccgcctcggccttccaaaa | 110 |
| 7 | 150863997 | tccaggcaggtgccgaggtgccgaggttccgagcaggttcctgtctggaat | 111 |
| 13 | 25744828 | ggccccggctcggcgcgccgatgccccgcggcgtcctctccccgggcgccg | 112 |
| 6 | 31869011 | ttcatgttccgtagcgttgcggcctcgtgccgggcagctggaagcgcagg | 113 |
| 18 | 74962154 | tgcgcggctgcagccggcggatccctcttccccaggctccgtggtcgcgcag | 114 |
| 7 | 100081899 | ggaaaaccggagcaggtatggaggccgcagcccagaaggtagcagtgggc | 115 |
| 17 | 79219936 | tcatgcgagggtcccccgtctctgctcctggccctgccacgagccagttgg | 116 |
| 8 | 145700725 | tcaggggcgcgcggtgccggccctgctgtccccgaagaaggacatttctg | 117 |
| 16 | 857342 | gcggtgtgaccctcgaaagctagacgtgcccaggaggcagcagcccaggcc | 118 |
| 1 | 155096885 | cgtgagccaccgtgcccggcctattttcaacttctgaaaaatgtgtgcac | 119 |
| 1 | 153652312 | gctggcacacccgtcccgccgcttagccgcagggcctcccctctgacctg | 120 |
| 16 | 30572707 | gggcgggcgccgctgagcgcgtctaggtggccgcaggtcgcggcatcgcgt | 121 |
| 17 | 7349079 | cagcgggtggaggttcggggctgggtggattatgagctgaaggcagggccg | 122 |
| 5 | 138720118 | gcagcttcatgccacagcactgagtccgcccgcctgccggtgtccacactg | 123 |
| 5 | 138720103 | ctctccagctgggcagcagcttcatgccacagcactgagtccgcccgcctg | 124 |
| 1 | 204159853 | ctggcttcctctcggtgcacggcaggctctgctcccgggggccaggaggc | 125 |
| 17 | 39684270 | ccagcagcccgtcggacgcggtcaggacgccgccgtagccgccgccgtagg | 126 |
| 17 | 39684420 | gcccaaaacgcacggagccgccgcccaggcctccgaaaggacgacgtggccg | 127 |
| 17 | 39684281 | tcggacgcggtcaggacgccgccgtagccgccgccgtaggccccccgaggag | 128 |
| 17 | 39684431 | acggagccgccgcccaggcctccgaaggacgacgtggccgacgactggcga | 129 |
| 5 | 76941587 | ccgccagcccggcccgctccgcctcggctgggcggccgggttggcacaagc | 130 |
| 19 | 38909058 | acctgtgcacgctgtagggggccgggacggctcagcaccatcacctgcacc | 131 |
| 17 | 38083480 | tccccgaagccgagccgctccccgcctcccaccccctagccgaggcgctcct | 132 |
| 11 | 67232339 | ccagagcccggtcagggcgaggggcggaggcttcgaggccttccgggctg | 133 |
| 11 | 65555542 | agacggtgggacaggcgcccgctgcgccccgcttgcccttaaagcagaggt | 134 |
| 4 | 184826958 | gcgcgctcgcgccggagcagcgctgccgccgcggcaggtcgatcgcaggc | 135 |
| 1 | 16344481 | ccaggcgggcgagggctggacaggagagggtgtgggcgcaggcctctgggc | 136 |
| 4 | 113559219 | cgcgggaggatcacttgaggtcaggagttcgagaccagcctggccaatatg | 137 |
| 3 | 147127933 | tcggcgtgaccacctttggcgcgtcccgccaccactccgcggggcgacgtgg | 138 |
| 19 | 49199977 | atcccggggaggtgcaggaagacagcgagctcgaggcagtggggtggact | 139 |
| 1 | 116371612 | gcccaccacacaccgagcccatccagggacacccgaacttcacattaaaca | 140 |
| 12 | 49736099 | cgtcactcagccggccgcccagggagctcctgggcccggcccgggagaggg | 141 |
| 4 | 113441952 | cccccttgcaacgctaggattcgttattgatagtggtgagcgctgggaatga | 142 |
| 3 | 128202153 | ttatcttcaggctgcagatgtccggataggaaactccggcaggagatccga | 143 |
| 3 | 128211103 | gacagatccagaacgccgtctacgccctaccggccgacagtcttcaagcccg | 144 |
| X | 142722093 | tcgcgctggcagcgctcgcctggctttgcagagcttttagagttacccacc | 145 |
| 19 | 58220456 | agacgctttcgtgcaggagggacgacgactcccctcacgccttcgtggccc | 146 |
| 8 | 496049 | caggttaattttttcccgcgacgcgcttcgtatcgcttcttacaccaaatat | 147 |
| 19 | 1071621 | cggggcctcccagcggcttcccggagctcctggagcccaatcccattccc | 148 |
| 19 | 1071671 | cggagtccgcctcgcatccagcagcgaagacatgttccggtccgggtctc | 149 |
| 8 | 98289816 | cacagtccaggggagccggcaggcggcctcctccccgagccggaggagct | 150 |
| 12 | 54379492 | cgccagcccgagctactccgcgctggacaagacgccccactgttctgggc | 151 |
| 6 | 3229090 | tgcagccagcgcgcgcgagacgaccccaagaccccacgcgcactcgcacgag | 152 |
| 8 | 144789578 | gccagtgactgcacgcgctgacgcgcctcgcgctcgaaggccgccttgtcc | 153 |
| 3 | 181430713 | acggcgcagcgcagatcagcccatgcaccgctacgacgtgagcgccctgc | 154 |
| 3 | 181437263 | agagccgacgcgcgggcaaattgaggccgagctgacgagctccggcgggtg | 155 |
| 12 | 57632109 | cgcctcactccggcggataatgagataaagtgtcagagacacggcgagaac | 156 |
| 14 | 105881108 | cgcgctcttcgcgggacggcagagggagggtctctgaggcgcgtggaatca | 157 |
| 8 | 53852540 | acgcgtcgactctggccgctgccggcgccgctggcggtggctgtaccag | 158 |
| 3 | 138664165 | gcgcgcagagaggcagcttcaggccaggggagtgcaaggtcacagaggtca | 159 |
| 4 | 3769374 | gccagctcgcgctccgtcgagttcttcctgtcgccgccgccgccgcaggca | 160 |
| X | 101410564 | ctccctcccgcggacctgcaggaagcaggctgtttccttcagtctcctcc | 161 |
| 11 | 1903324 | cgggaggacgcactttccagatgtggggatgtgtgtgcctgtctcaacccc | 162 |
| 3 | 194407921 | gccgaggagcgcgcgctgcgccgcccgggccacctctacctgctgcaccgc | 163 |
| 14 | 105962141 | aggcccgccctctccccgaagctgtgtgcggcactggccaggtggactgg | 164 |
| 12 | 57632111 | cctcactccggcggataatgagataaagtgtcagagacacggcgagaacaa | 165 |

TABLE 1-continued

Chromosome (Chr), location, and sequences of SEQ ID NOS: 1-219.

| Chr | Location | Sequence | SEQ ID NO: |
|---|---|---|---|
| 19 | 46285563 | tccaacaccagctgctggagccgcctcagccgcacctcggctgacatgttg | 166 |
| 1 | 16344465 | cggcgccgggccctgcccaggcgggcgagggctggacaggagagggtgtgg | 167 |
| 10 | 129534298 | tacccagggcgaggccagcttccaggaggtcagcgccaacaccgccggcag | 168 |
| 10 | 129535498 | ggtgcggcaccgctggcccaggcccgggcgcggctggacatggccacctac | 169 |
| 1 | 1141912 | cagggcccgaaacgcgcccatcgcccgtgctgtgccatgctcgggtttca | 170 |
| 1 | 63795329 | agggttgagaggagaagggaaagacagacacagacgcgccgggccggtgga | 171 |
| 1 | 223306673 | ttgaatatgctgcaaaacatccacagagcctcaaagcgagctcggaacctg | 172 |
| 1 | 1946129 | attcaaattgccactttaaaaaacatagaaccgagaatagaataccgact | 173 |
| 4 | 185942444 | ggcgcccgtcctacccggagccaagtgcccgacgcgcgcgcaccgcacgcc | 174 |
| 10 | 124899787 | gccgccgcgctcttagtgagcagcctgcggaggcacagcgcgccggaaccg | 175 |
| 16 | 2029714 | ccgcggtgcttctggcccagtcttgccacacggtcaagccgcagtggtggc | 176 |
| X | 153707116 | gcccggacctggcgcgtgcgctgggggagctccaccggccgggagctgcggc | 177 |
| 14 | 102026587 | cttgacgcgtccgggcgcctccgcggtgagtcgcgccgcgctctcggggt | 178 |
| 14 | 102027837 | ctcgccaggccacgtcgcggttggtggtcggagagggcgaggggtcccagg | 179 |
| 1 | 207818668 | ttctccggtaggaccccggggtggattcgcgcgtccgcggcgaggctagag | 180 |
| 1 | 2461899 | cgcggcacaatgtccgggctgtgggaacgcgctcgccctcattagcatccc | 181 |
| 12 | 104609456 | atgacttcgctgttgtcaccgagcgccccgcccaccgcgttctccgacccg | 182 |
| 12 | 104609706 | acgggccgaagcgggccttccggccggggttgggggataaagtgccccggag | 183 |
| X | 135068097 | tccttccatttctgcctcgccttcccctacccgcgttttctctgcctca | 184 |
| 6 | 43478451 | atccgcgccgcgcctcgctcccgcccccgtgactcgaggcgcagcgtgcgt | 185 |
| 17 | 72353473 | gcgcagcgcccgctcggccacggcagggggcggcgcgcgcgaccagcca | 186 |
| 6 | 31869013 | catgttccgtagcgttgcggcctcgtggccgggcagctggaagcgcaggac | 187 |
| 3 | 138664125 | gagacgctggggctccggaaagagacgagcccagtagaaagcgcgcagaga | 188 |
| 14 | 105962153 | ctcccccgaagctgtgtgcggcactggccaggtggactggggccatggctgg | 189 |
| 1 | 6520349 | ccccgtatcccccagcccttggcaacactggagtgcacacgccgccacggt | 190 |
| 2 | 175202273 | gggcgagaggcgcgagcacacaagcgagtagagacaccgagaacgaacgag | 191 |
| 2 | 175205523 | gcgcgtgggaggcgagatcccgccagttacaacacgagttcggtccccaat | 192 |
| 7 | 155166720 | cacggcctcgccctgggcgcggggcatcaccggcgcggaggcccgagggcg | 193 |
| 6 | 33048502 | gcttcctggagagatacatctacaaccgggaggagttcgcgcgcttcgaca | 194 |
| 6 | 33048552 | agcgacgtgggggagttccgggcggtgacggagctggggcggcctgctgcg | 195 |
| 17 | 79219938 | atgcgagggtcccccgtctctgctcctggccctgccacgagccagttggct | 196 |
| 2 | 241856151 | tgccggggggagcgcagggcgggagctgctgagcaggcggagggagggcgg | 197 |
| 14 | 36989316 | actgcctccggaccacatcgggcttcgctgcgctgagcccagtcgccaac | 198 |
| 16 | 83848047 | tcacaaacacagctgaccgtctcacagctgcacacctgcaccgctcacgag | 199 |
| 11 | 123892846 | tttaagttttcccacgagcaaggcagcgaaaatagaatgtggtagatagaa | 200 |
| X | 100645911 | gccttacactctatgattgctcctaccgactcccatgaggaagtgcgatcg | 201 |
| 7 | 27204917 | cgggctgaagtcggggtgctcggccagcgtcgccgcctgccggggaggctg | 202 |
| 7 | 27205067 | ggtggccatcaccgtgcccagcgcctggcccgcccggcccgacccacggaa | 203 |
| 11 | 65555562 | gctgcgccccgcttgcccttaaagcagaggtgggatcgggtctcacctctg | 204 |
| 11 | 123892831 | tcttggtgttttttttttaagttttcccacgagcaaggcagcgaaaataga | 205 |
| 11 | 2907637 | ctgctgctgggctggtgtcccttcgagggctccgcgcgcctggagccctca | 206 |
| 8 | 144789585 | actgcacgcgctgacgcgcctcgcgctcgaaggccgccttgtcctccagga | 207 |
| 12 | 58120953 | gcggcgccaggaacagtagctgctcgtacttggcgcgaatccacgactcgc | 208 |
| 19 | 19971844 | gctctcgtgatgtccgacggcactcaccattctaggcttccaggaggtcc | 209 |
| 14 | 102026583 | cgcacttgacgcgtccgggcgcctccgcggtgagtcgcgccgcgctctcg | 210 |
| 14 | 102027833 | atgcctcgccaggccacgtcgcggttggtggtcggagagggcgaggggtcc | 211 |
| 16 | 30572707 | gggcgggcgccgctgagcgcgtctaggtggccgcaggtcgcggcatcgcgt | 212 |
| 8 | 67874363 | cccggcacgcacgagaggtggcgcggctccttctcgccgacgccgcggaaa | 213 |
| 8 | 67874713 | gtgacttttatgcgggcgccccgcgggccaggcgtgtgtgctccgaccggct | 214 |
| 19 | 46285551 | aggaagcccggtccaacaccagctgctggagccgcctcagccgcacctcg | 215 |
| 20 | 30312200 | gaggccgaggcgggcggatcacctgaggttaggagttcaagaccagcgtgg | 216 |
| 17 | 72353304 | cgctgccgttgacgtcgaagaacttggcgtagtgcagcggcgacgcggcgt | 217 |
| 17 | 72353454 | tcatggggtagcgtatggcgcgcagcgcccgctcggccacggcaggggggcg | 218 |
| 2 | 39187663 | gccgagcgcgccgcgcaggcgcacggcccggccgccgccgcgtcgccgcc | 219 |

The sequences are presented as found in the human genome sequence hg19 (version GRCh37/hg19). The genomic coordinates (location) provided above correspond to the forward strand and are counted from the beginning of the chromosome.

Table 1 provides the location of MR represented by SEQ ID Nos. 1-219. The corresponding sequences may also be obtained from the MRs' locations from public databases such as the National Center for Biotechnology Information's database (ENTREZ), the European Molecular Biology Laboratory (EMBL) Nucleotide Sequence Database (also known as EMBL-Bank), and the University of California Santa Cruz (UCSC) Genome Browser.

The one or more MRs may be any segment of the one or more SEQ ID NOS:1-219 presented in Table 1. A segment is a representative number of nucleotide residues encompassing a CpG methylatable island, i.e., a CG sequence. For example, a segment may be 3, 4, 5, 6, 7, 8, 9, 10, . . . , 45, 46, 47, 48, 49, 50, 51, 52, 53, 54, or 55 nt in length.

1. Biomarker Methylation

The biomarker for breast cancer may have epigenetic alterations, such as one or more nucleotide residues in the biomarker may be methylated.

DNA methylation is a process by which methyl groups are added to the DNA molecule. Methylation can change the activity of a DNA segment without changing the sequence. When located in a gene promoter, DNA methylation typically acts to repress gene transcription. Two of DNA's four bases, cytosine (C) and adenine (A), can be methylated. Cytosine methylation is widespread in both eukaryotes and prokaryotes, even though the rate of cytosine DNA methylation can differ greatly between species.

CpG sites (or CG sites) are regions of DNA where a cytosine nucleotide is followed by a guanine nucleotide in the linear sequence of bases along its 5'→3' direction. CpG is shorthand for 5'-C-phosphate-G-3', that is, cytosine and guanine separated by only one phosphate group. In mammals, DNA methylation is almost exclusively found in CpG dinucleotides, with the cytosines on both strands being usually methylated. Non-CpG methylation may be observed in embryonic stem cells.

Epigenetic alterations are among the most common molecular abnormalities in human cancers. DNA methylation does not change the genomic DNA sequence and is a form of epigenetic alteration (Visvanathan et al., *J Clin Oncol* 35:751-758 (2016)).

The most widely studied epigenetic alteration to date is the methylation (5-methylcytosines) of DNA at the CpG dinucleotides, which are highly concentrated in the CpG islands within the promoter region or near the first exon. Varying degrees of methylation within a gene's CpG islands leads to various levels of gene silencing, and in cancer, promoter hypermethylation has been linked to the silencing of tumor suppressor genes and subsequent oncogenesis. Screening for gene mutations is a common practice to test for an individual's predisposition to cancer but cannot reflect the current status or activity of disease (Leygo et al., *Disease Markers,* 2017, Article ID 3726595 (2017)).

2. Informative Regions

In some aspects, the segment of the MR that is methylatable and is informative for an aspect of BC may be shorter than 50 nt. The informative region typically defines the shortest methylatable region in any one of SEQ ID NOS:1-219 that is informative for an aspect of BC. For example, the segment of 1, 2, 3, 4, 5, 6, 7, 8, 9, 10, . . . , 45, 46, 47, 48, 49, or 50 nt in length of any one of SEQ ID NOS:1-219 may be the informative region. Therefore, the informative region within one or more of SEQ ID NOS:1-219 is at least or no more than 1, 2, 3, . . . , 48, 49, or 50 nucleotides in length.

B. Flanking Regions Surrounding Methylatable Regions

The MRs may be the one or more SEQ ID NOS: 1-219 and their 5' and/or 3' flanking regions.

The DNA sequences extending on either side of a specific locus or sequence may be described as the flanking region. The length of the flanking region is typically dependent on the needs of the test being conducted.

Flanking sequences to the DNA segment presented in Table 1 are known or may be known by those of skill in the art from representative DNA sequence databases. Flanking regions are typically identified as 5' or 3' flanking regions. For example, the 5' flanking region of a DNA sequence is a region of DNA that is immediately adjacent to the 5' end of the sequence. The 3' flanking region of a DNA sequence is a region of DNA that is immediately adjacent to the 3' end of the sequence.

The MRs may be the one or more SEQ ID NOS: 1-219 as presented in Table 1 and their 5' and/or 3' flanking regions. The flanking regions are generally flanking sequences extending up to but not including a first encountered methylated residue.

III. Methods of Using

Generally, quantification of methylation level of a biomarker includes the steps of analyzing isolated DNA from a sample of the subject for DNA methylation, and recording the number and/or position of one or more methylated nucleotide residues in the epigenetic biomarker. The methods allow diagnosis of BC in a subject with a specificity of at least 90% and up to 100% and a sensitivity of at least 90%, more preferably, with a sensitivity of at least 94%, for example 94%, 95%, 96% etc., up to, 100%. Screening of breast cancer at the whole population level is carried out using mammography, which has a sensitivity and specificity greater than 70% and 85% with larger tumors. Leygo, et al., Disease Markers Volume 2017, Article ID 3726595 https://doi.org/10.1155/2017/3726595). Conclusive detection is preferably done by histopathology. Techniques such as fine needle aspiration (FNA) and a core biopsy are required for the extraction of suspected tumor tissue and subsequent histological evaluation.

A. Samples

Generally, any sample obtained from a subject may be used to isolate the DNA of the subject. Typically, the samples are obtained via a non-invasive or minimally invasive procedure. The sample may be provided by the subject. The sample may be produced by, synthesized, secreted, or derived, at least in part, from the cells of the subject and is used to determine presence or absence of a disease, the severity of the disease, or disease prognosis.

The sample obtained from the subject may be tissue, cells, and/or a bodily fluid. For example, the sample may be cells, tissue, serum, plasma, urine, spittle, sputum, and stool. The sample may be any sample containing DNA from the tumor.

The methods may employ assaying tissue, blood, serum, plasma, spittle, stool, urine, or any other body fluid containing tumor DNA directly. Methods to assess the epigenetic biomarker directly in a bio-specimen are known in the art. Alternatively, the DNA from the subject's sample may be extracted (isolated) and the extracted DNA and nucleic acids can be concentrated for quantifying the methylation level of the isolated DNA.

B. DNA Isolation

Methods of DNA isolation are known in the art. DNA may be isolated from any one of tissues, cells, blood, urine, spittle, sputum, and stool using similar methods. The methods typically include a step of breaking open cells (if any), and then isolating and concentrating the nucleic acids using reagents, spin columns, or beads.

For example, any one of silica chromatography, silica beads, phenol chloroform method, or any bead or column method may be used to concentrate nucleic acids and isolate the DNA from the sample for further analyses.

C. Methylation Level Quantification

The term "methylation level" of an MR refers to the number of methylated residues in an MR, the position of the methylated residues in an MR, or both. The methylation level may be detected by absolute quantification or relative quantification. The methylation level of a biomarker may be used to determine the mSCORE for the subject.

1. Absolute Quantification

The methylation level may be detected by absolute quantification, such as by detecting the number of methylated nucleotide residue(s) in the epigenetic biomarker, the position of methylated nucleotide residue(s) in the epigenetic biomarker, both the number and the position of methylated nucleotide residue(s) in the epigenetic biomarker, The methylation level of epigenetic biomarkers in a BC-free subject may be between 0 and 23.

2. Relative Quantification

The DNA methylation level of the epigenetic biomarker in the subject may be detected by a relative quantification. The relative quantification may include determining the methylation level in the subject and in a control subject (known to be BC-free; or control subject known to have BC diagnosis). The method may further include comparing the DNA methylation level of the same subject obtained at two or more different time points, to a methylation level of a different subject, or to a methylation level of a control subject.

For example, the DNA methylation level in the subject may be detected to be at the same level as that of the control subject known to be BC-free. This quantification may indicate that the subject is also BC-free. The DNA methylation level in the subject may be detected to be at a level below that of the control subject known to be BC-free. This quantification may also indicate that the subject is also BC-free. Alternatively, the DNA methylation level in the subject may be detected to be at a level above that of the control subject known to be BC-free. This quantification may also indicate that the subject has BC, or should undergo additional diagnostic tests to confirm that the subject has BC.

3. mSCORE

The methylation level of the one or more biomarkers may be included in determining the methylation score (mSCORE) of the subject. The method generally includes obtaining the total methylation (mTOT) for the subject, the mTOT represented by the sum of the methylation levels of all 219 MRs considered for the subject; obtaining coverage (COV) for the subject, the COV represented by the number of MRs for the subject containing at least one methylated residue; and calculating the mSCORE from Equation (1):

$$mSCORE = COV \times mTOT \quad \text{Equation (1)}.$$

To compute the mSCORE, the measurements provide the number of methylated nucleotides within individual MRs. Typically, there is a specific value to the mSCORE that can be compared to the mSCORE of a normal or control subjects (subjects that are cancer-free, for example in the same age range). In other aspects, the mSCORE may be compared in a relative way, for example, an increase or a decrease in an mSCORE due to a treatment, within the same subject.

The mSCORE may be any value between 0 and 39,000 or more. Exemplary values for the mSCORE are presented in Table 2. The mSCORE value of about 199 may serve as a threshold value for diagnosing the subject with very high accuracy of having or developing BC.

4. Methylation Quantification Assays

Analyzing the subject's isolated DNA for DNA methylation level may include subjecting the isolated DNA to methylation quantification assays, such as Combined Bisulfite Restriction Analysis (COBRA), MethyLight, methylation-sensitive single-nucleotide primer extension (Ms-SNuPE), methylated CpG island amplification (MCA), Methyl-BEAMing, and methylation-specific polymerase chain reaction (MSP).

The methylation level can be determined by any suitable means of the art, although in specific embodiments the methylation level is determined with methylation-specific PCR (including probe-based real-time PCR for methylation analysis; (Herman et al., 1996; God et al., 2004; Ishiguro et al., 2006) (such as MethyLight PCR (QIAGEN®; Applied Biosystems®, Roche® Diagnostics)); methylation microarrays from Illumina®, Epigenetic & Specialty Microarrays from Agilent Technologies, Inc, or microarray chips from Affymetrix™ (Thermo Fisher Scientific®)); methylation sequencing (including bisulfite DNA sequencing; see Ballot et al., 2003; and Oster et al., 2011; Kim et al., 2011, for example); methyl-beaming (Li, et al., *Nature Biotechnol.* 2009, 27(9): 858-863), mass spectrometry; or a combination of these assays (Fernandez, et al. *Methods Mol Biol.* 2018; 1708:49-58; PMID: 29224138). In some methods, quantity of DNA is required for comparison, and there are standard means in the art for identifying DNA quantity, including spectrophotometry and/or gel electrophoresis, for example.

A part of the analysis of methylation may include bisulfite genomic sequencing, whether by Sanger sequencing or NGS (Next Generation Sequencing) or any other technology. Accordingly, denatured genomic DNA can be treated with freshly prepared bisulfite solution at 55° C. in the dark overnight (or only incubation for 3 hours), followed by column purification and NaOH treatment, for example. Bisulfite treatment modifies DNA converting un-methylated, but not methylated, cytosines to uracil (Chatterjee et al. *Nucleic Acids Res.* 2012 May; 40(10):e79. doi: 10.1093/nar/gks150. Epub 2012 Feb. 16).

The term "modifies"—as used in this section—refers to the conversion of an un-methylated cytosine to another nucleotide that will distinguish the un-methylated from the methylated cytosine. Preferably, the agent modifies un-methylated cytosine to uracil. Preferably, the agent used for modifying un-methylated cytosine is sodium bisulfite, however, other agents that similarly modify un-methylated cytosine, but not methylated cytosine can also be used or any method allowing the distinguishing between the methylated cytosine and the un-methylated cytosine. Sodium bisulfite (NaHSO3) reacts readily with the 5,6-double bond of cytosine, but poorly with methylated cytosine. Cytosine reacts with the bisulfite ion to form a sulfonated cytosine reaction intermediate that is susceptible to deamination, giving rise to a sulfonated uracil. The sulfonate group can be removed under alkaline conditions, resulting in the formation of uracil. Uracil is recognized as a thymine by Taq polymerase and therefore upon PCR, the resultant product contains cytosine only at the position where 5-methylcytosine occurs in the starting template DNA.

In some embodiments, methylation assays allow for determination of the methylation state of one or a plurality of CpG dinucleotides within a DNA sequence. Such assays involve, among other techniques, DNA sequencing of bisulfite-treated DNA, PCR (for sequence-specific amplification), Southern blot analysis, use of methylation-sensitive restriction enzymes, etc. For example, genomic sequencing has been simplified for analysis of DNA methylation patterns and 5-methylcytosine distribution by using bisulfite treatment (Frommer et al., *Proc. Natl. Acad. Sci. USA* 89:1827-1831, 1992). Additionally, restriction enzyme digestion of PCR products amplified from bisulfite-converted DNA is used, e.g., the method described by Sadri and Homsby, *Nucl. Acids Res.* 24:5058-5059, 1996, or Combined Bisulfite Restriction Analysis (COBRA) (Xiong and Laird, *Nucleic Acids Res.* 25:2532-2534, 1997).

Combinations of multiple methods for quantifying methylation may be employed.

a. COBRA

Combined Bisulfite Restriction Analysis (COBRA) analysis is a quantitative methylation assay useful for determining DNA methylation levels at specific genomic loci in small amounts of genomic DNA (Xiong and Laird, *Nucleic Acids Res.* 25:2532-2534, 1997). Restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al., *Proc. Natl. Acad. Sci. USA* 89:1827-1831, 1992. PCR amplification of the bisulfite converted DNA is then performed using primers specific for the interested MRs, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from micro-dissected paraffin-embedded tissue samples or body fluids circulating DNA. Typical reagents (e.g., as might be found in a typical COBRA-based kit) for COBRA analysis may include, but are not limited to: PCR primers for specific MR (or methylation-altered DNA sequence or CpG island); restriction enzyme and appropriate buffer; gene-hybridization oligo; control hybridization oligo; kinase labeling kit for oligo probe; and radioactive nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

b. MethyLight

The MethyLight assay is a high-throughput quantitative methylation assay that utilizes fluorescence-based real-time PCR (TaqMan®) technology that requires no further manipulations after the PCR step (Eads et al., *Cancer Res.* 59:2302-2306, 1999). The MethyLight process begins with a mixed sample of genomic DNA that is converted, in a sodium bisulfite reaction, to a mixed pool of methylation-dependent sequence differences according to standard procedures. The bisulfite process converts un-methylated cytosine residues to uracil. Fluorescence-based PCR is then performed either in an "unbiased" (with primers that do not overlap known CpG methylation sites) PCR reaction, or in a "biased" (with PCR primers that overlap known CpG dinucleotides) reaction. Sequence discrimination can occur either at the level of the amplification process or at the level of the fluorescence detection process, or both.

The MethyLight assay may be used as a quantitative test for methylation patterns in the genomic DNA sample, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe overlie any CpG dinucleotides. Alternatively, a qualitative test for genomic methylation is achieved by probing of the biased PCR pool with either control oligonucleotides that do not "cover" known methylation sites (a fluorescence-based version of the "MSP" technique), or with oligonucleotides covering potential methylation sites.

The MethyLight process can be used with a "TaqMan®" probe in the amplification process. For example, double-stranded genomic DNA is treated with sodium bisulfite and subjected to one of two sets of PCR reactions using TaqMan® probes; e.g., with either biased primers and TaqMan® probe, or unbiased primers and TaqMan® probe. The TaqMan® probe is dual-labeled with fluorescent "reporter" and "quencher" molecules, and is designed to be specific for a relatively high GC content region so that it melts out at about 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system.

Typical reagents (e.g., as might be found in a typical MethyLight-based kit) for MethyLight analysis may include, but are not limited to: PCR primers for specific MR (or methylation-altered DNA sequence or CpG island); TaqMan® probes; optimized PCR buffers and deoxynucleotides; and Taq polymerase.

c. MsSNuPE

The methylation-sensitive single-nucleotide primer extension (Ms-SNuPE) technique is a quantitative method for assessing methylation differences at specific CpG sites based on bisulfite treatment of DNA, followed by single-nucleotide primer extension (Gonzalgo and Jones, *Nucleic Acids Res.* 25:2529-2531, 1997). Briefly, genomic DNA is reacted with sodium bisulfite to convert un-methylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest Small amounts of DNA can be analyzed (e.g., microdissected pathology sections), and it avoids utilization of restriction enzymes for determining the methylation level at CpG sites. Typical reagents (e.g., as might be found in a typical Ms-SNuPE-based kit) for Ms-SNuPE analysis may include, but are not limited to: PCR primers for specific gene (or methylation-altered DNA sequence or CpG island); optimized PCR buffers and deoxynucleotides; gel extraction kit; positive control primers; Ms-SNuPE primers for specific gene; reaction buffer (for the Ms-SNuPE reaction); and radioactive nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

d. MCA

The methylated CpG island amplification (MCA) technique is a method that can be used to screen for altered methylation patterns in genomic DNA, and to isolate specific sequences associated with these changes (Toyota et al., *Cancer Res.* 59:2307-12, 1999). Briefly, restriction enzymes with different sensitivities to cytosine methylation in their recognition sites are used to digest genomic DNAs from primary tumors, and normal tissues prior to arbitrarily primed PCR amplification. Fragments that show differential methylation are cloned and sequenced after resolving the PCR products on high-resolution polyacrylamide gels. The cloned fragments are then used as probes for Southern analysis to confirm differential methylation of these regions. Typical reagents (e.g., as might be found in a typical MCA-based kit) for MCA analysis may include, but are not limited to: PCR primers for arbitrary priming Genomic DNA; PCR buffers and nucleotides, restriction enzymes and appropriate buffers; gene-hybridization oligos or probes; control hybridization oligos or probes.

e. Methyl-BEAMing

In BEAMing, PCR amplification of individual DNA molecules takes place within aqueous nano-compartments suspended in a continuous oil phase. Each aqueous nano-compartment contains the DNA polymerase, cofactors, and dNTPs required for PCR. When a compartment contains a single DNA template molecule as well as a bead, the PCR product within the compartment becomes bound to the bead. Each bead thereby ends up with thousands of identical copies of the template within its nano-compartment a process similar to that resulting from cloning an individual DNA fragment into a plasmid vector to form a bacterial colony. After PCR, the beads are collected by breaking the emulsion and their status is individually assessed by incubation with fluorescent hybridization probes. In MethylBEAMing, the status of harvested beads is interrogated by fluorescent probes that specifically hybridize to either methylated or un-methylated derived sequences, with flow-cytometry providing an accurate enumeration of the fraction of original template molecules that were methylated or un-methylated within the queried sequence (Li et al., *Nature Biotechnology*, 27(9):858-863 (2009)).

f. MSP

Another method for determining the methylation level of the epigenetic biomarkers is methylation-specific polymerase chain reaction (MSP).

One embodiment provides a method for detecting a methylated CpG-containing nucleic acid, the method including contacting a nucleic acid-containing specimen with an agent that modifies un-methylated cytosine; amplifying the CpG-containing nucleic acid in the specimen by means of CpG-specific oligonucleotide primers; and detecting the methylated nucleic acid. It is understood that while the amplification step is optional, it is desirable in the preferred method.

Some primers used in the disclosure for amplification of the CpG-containing nucleic acid in the specimen, after bisulfite modification, specifically distinguish between methylated and non-methylated DNA, in particular embodiments of the disclosure. Two exemplary types of primers could be designed: one set recognizing methylated cytosine and the other set targeting the un-methylated cytosine. The first set of primers enables one to assess the methylation; however, the second set enables one to quantify the un-methylated DNA. MSP primers for the non-methylated DNA preferably have a T in the 3' CG pair to distinguish it from the C retained in methylated DNA, and the complement is designed for the antisense primer. MSP primers usually contain relatively few Cs or Gs in the sequence since the Cs will be absent in the sense primer and the Gs absent in the antisense primer (C becomes modified to U (uracil) which is amplified as T (thymidine) in the amplification product).

The primers of the disclosure embrace oligonucleotides of sufficient length and appropriate sequence so as to provide specific initiation of polymerization on a significant number of nucleic acids in the polymorphic locus. Specifically, the term "primer" as used herein refers to a sequence containing two or more deoxyribonucleotides or ribonucleotides, in certain cases more than three, and in particular cases more than 8, which sequence is capable of initiating synthesis of a primer extension product, which is substantially complementary to a polymorphic locus strand. Environmental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. In particular cases, the primer is an oligodeoxy ribonucleotide. The primer must be sufficiently long to prime the synthesis of extension products in the presence of the inducing agent for polymerization. The exact length of primer will depend on many factors, including temperature, buffer, and nucleotide composition. The oligonucleotide primer typically contains 12-20 or more nucleotides, although it may contain fewer nucleotides.

Primers of the disclosure are designed to be "substantially" complementary to each strand of the genomic locus to be amplified and include the appropriate G or C nucleotides as discussed above. This means that the primers must be sufficiently complementary to hybridize with their respective strands under conditions that allow the agent for polymerization to perform. In other words, the primers should have sufficient complementarity with the 5' and 3' flanking sequences to hybridize therewith and permit amplification of the genomic locus.

Oligonucleotide primers of the disclosure are employed in the amplification process that is an enzymatic chain reaction that produces exponential quantities of target locus relative to the number of reaction steps involved. Typically, one primer is complementary to the negative (−) strand of the locus and the other is complementary to the positive (+) strand. Annealing the primers to denatured nucleic acid followed by extension with an enzyme, such as the large fragment of DNA Polymerase I and nucleotides, results in newly synthesized + and − strands containing the target locus sequence. Because these newly synthesized sequences are also templates, repeated cycles of denaturing, primer annealing, and extension results in exponential production of the region (i.e., the target locus sequence) defined by the primer. The product of the chain reaction is a discrete nucleic acid duplex with termini corresponding to the ends of the specific primers employed.

The oligonucleotide primers of the disclosure may be prepared using any suitable method, such as conventional phosphotriester and phosphodiester methods or automated embodiments thereof. In one such automated embodiment, diethylphosphoramidites are used as starting materials and may be synthesized as described by Beaucage, et al., *Tetrahedron Letters*, 22:1859-1862, 1981. One method for synthesizing oligonucleotides on a modified solid support is described in U.S. Pat. No. 4,458,066.

Any nucleic acid specimen, in purified or non-purified form, can be utilized as the starting nucleic acid or acids, provided it contains, or is suspected of containing, the specific nucleic acid sequence containing the target locus (e.g., CpG). Thus, the process may employ, for example, DNA or RNA, including messenger RNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid that contains one strand of each may be utilized. A mixture of nucleic acids may also be employed, or the nucleic acids produced in a previous amplification reaction herein, using the same or different primers may be so utilized. The specific nucleic acid sequence to be amplified, i.e., the target locus, may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA.

The nucleic acid-containing specimen used for detection of methylated CpG may be from any source including brain, colon, urogenital, hematopoietic, thymus, testis, ovarian, uterine, prostate, breast, colon, lung and renal tissue and may be extracted by a variety of techniques such as that described by Maniatis, et al., Molecular Cloning: A Laboratory Manual, Cold Spring Harbor, N.Y., pp 280, 281, 1982.

If the extracted sample is impure (such as plasma, serum, or blood or a sample embedded in paraffin), it may be treated before amplification with an amount of a reagent effective to open the cells, fluids, tissues, or animal cell membranes of the sample, and to expose and/or separate the strand(s) of the nucleic acid(s). This lysing and nucleic acid denaturing step to expose and separate the strands will allow amplification to occur much more readily.

Where the target nucleic acid sequence of the sample contains two strands, it is necessary to separate the strands of the nucleic acid before it can be used as the template. Strand separation can be effected either as a separate step or simultaneously with the synthesis of the primer extension products. This strand separation can be accomplished using various suitable denaturing conditions, including physical, chemical, or enzymatic means, the word "denaturing" includes all such means. One physical method of separating nucleic acid strands involves heating the nucleic acid until it is denatured. Typical heat denaturation may involve temperatures ranging from about 80 to 100° C., for times ranging from about 15 seconds to 10 minutes. Strand separation may also be induced by an enzyme from the class of enzymes known as helicases or by the enzyme RecA, which has helicase activity, and in the presence of riboATP, is known to denature DNA. The reaction conditions suitable for strand separation of nucleic acids with helicases are described by Kuhn Hoffmann-Berling, CSH-'Quantitative Biology, 43:63, 1978, and techniques for using RecA are reviewed in C. Radding, Ann. Rev. Genetics, 16:405-437, 1982.

When complementary strands of nucleic acid or acids are separated, regardless of whether the nucleic acid was originally double or single stranded, the separated strands are ready to be used as a template for the synthesis of additional nucleic acid strands. This synthesis is performed under conditions allowing hybridization of primers to templates to occur. Generally synthesis occurs in a buffered aqueous solution, preferably at a pH of 7-9, most preferably about 8. Preferably, a molar excess (for genomic nucleic acid, usually about 108:1 primer: template) of the two oligonucleotide primers is added to the buffer containing the separated template strands. As a practical matter, however, the amount of primer added will generally be in molar excess over the amount of complementary strand (template) when the sequence to be amplified is contained in a mixture of complicated long-chain nucleic acid strands. Large molar excess is preferred to improve the efficiency of the process.

The deoxyribonucleoside triphosphates dATP, dCTP, dGTP, and dTTP are added to the synthesis mixture, either separately or together with the primers, in adequate amounts and the resulting solution is heated to about 90-100° C. from about 15 seconds to 10 minutes, preferably from 1 to 4 minutes. After this heating period, the solution is allowed to cool to hybridization temperature primers specific Tm, which is preferable for the primer hybridization. To the mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at Tm temperature up to a temperature above which the agent for polymerization no longer functions.

The agent for polymerization may be any compound or system, which will function to accomplish the synthesis of primer extension products, including enzymes. Suitable enzymes for this purpose include, for example, E. coli DNA polymerase I, Klenow fragment of E. coli DNA polymerase I, T4 DNA polymerase, other available DNA polymerases, polymerase muteins, reverse transcriptase, and other enzymes, including heat-stable enzymes (i.e., those enzymes which perform primer extension after being subjected to temperatures sufficiently elevated to cause denaturation). Suitable enzymes will facilitate combination of the nucleotides in the proper manner to form the primer extension products that are complementary to each locus nucleic acid strand.

Generally, the synthesis will be initiated at the 3' end of each primer and proceed in the 5' direction along the template strand, until synthesis terminates, producing molecules of different lengths. There may be agents for polymerization, however, which initiate synthesis at the 5' end and proceed in the other direction, using the same process as described above.

In some embodiments, the method of amplifying is by PCR, as is commonly used by those of ordinary skill in the art. Alternative methods of amplification have been described and can also be employed as long as the methylated and non-methylated loci amplified by PCR is similarly amplified by the alternative.

The amplified products may be identified as methylated or non-methylated by sequencing. The amplified sequences can be further evaluated, detected, cloned, sequenced, and the like, either in solution or after binding to a solid support, by any method usually applied to the detection of a specific DNA sequence such as PCR, oligomer restriction (Saiki, et al., Rio/Technology, 3:1008-1012, 1985), allele-specific oligonucleotide (ASO) probe analysis (Conner, et al., Proc. Natl. Acad. Sci. USA, 80:278, 1983), oligonucleotide ligation assays (OLAs) (Landegren, et al., Science, 241:1077, 1988), and the like. Molecular techniques for DNA analysis have been reviewed (Landegren, et al., Science, 242:229-237, 1988).

Optionally, the methylation pattern of the nucleic acid can be confirmed by restriction enzyme digestion and Southern blot analysis. Examples of methylation sensitive restriction endonucleases that can be used to detect 5'CpG methylation include SmaI, SacII, EagI, MspI, HpaII, BstUI and BssHII, for example.

The amplified products may be quantitatively assessed for methylation by sequencing, using for example, capillary sequencing, (briefly, the treated amplified DNA is amplified by either forward or reverse primers in the presence of di-deoxyribonucleotides that stop the sequencing reaction and subjected to capillary electrophoresis to read the target sequence), high-throughput sequencing (sequencing by synthesis (Applied Biosystems®), pyrosequencing (454 Roche® Diagnostics) or by other technologies such as from Illumina®, Pacific Bio and Helicos.

D. Chips for Methylation Quantification

Also described are substrates for use in methylation level analysis.

Typically, a substrate includes linked, attached, or embedded nucleic acids, each containing part or all of MRs. A substrate may include nucleic acids that are complementary to part or all of MRs. The substrate may be a chip or a microchip.

Generally, the one or more nucleic acid sequences are complementary to all or to a portion of the sequence in any one of SEQ ID NOS:1-219. The one or more nucleic acid sequences may be attached at addressable locations on the substrate. The one or more nucleic acid sequences attached to the substrate permit hybridization of any sequence from SEQ ID NOS:1-219. The one or more nucleic acid sequences attached to the substrate permit PCR capture and bisulfite sequencing of any sequence from SEQ ID NOS:1-219.

IV. Methods of Using the Biomarker Methylation Level

Methods of detecting a DNA methylation level of an epigenetic biomarker in a subject, and using the methylation level for screening, diagnosing, or prognosing of breast cancer, are describes. The methods generally include analyzing isolated DNA from a sample of the subject for DNA methylation, recording the number and/or position of one or more methylated nucleotide residues in the epigenetic biomarker, and evaluating a breast cancer risk in a subject, or diagnosing a subject with breast cancer. These methods generally include determining the methylation level and/or the mSCORE of the subject and evaluating the subject for a risk of developing breast cancer, diagnosing the subject with breast cancer, or determining a risk of recurrence and disease prognosis in the subject.

A. Subjects

A subject may be a mammal, such as a domestic animal, farm animal, laboratory animals, non-human primate, or a human. The subject may be a human aged 50 years or older. The subject may have a desire or a need to know whether the subject has or is at risk of having BC, or is in need of prognosis or response to treatment in BC. The subject may have one or more symptoms of BC or may be asymptomatic for BC. In some cases, the subject has a prior history of having cancer, including a prior history of having BC.

In cases where a subject has one or more symptoms of a BC, the subject's DNA may be used in methods and/or with compositions of the disclosure. In specific cases, the subject has one or more symptoms such as swelling of all or part of the breast, skin irritation or dimpling, breast pain, nipple pain or the nipple turning inward, redness, scaliness, or thickening of the nipple or breast skin, a nipple discharge other than breast milk, a lump in the underarm area, weight loss, fatigue, anemia, and a combination thereof.

The subject may undergo one or more additional assays for determining BC in addition to the methods and/or compositions of the disclosure. Although any other assay may be employed, in some cases the one or more additional assays include ONCOTYPE® (Genomic Health, Inc., Redwood City, Calif.), Her2 status, MAMMAPRINT® (Agendia BV LLC, Amsterdam, Netherlands), hormone receptor status, carcinoembryonic antigen (CEA) tests, and combinations thereof. The additional assays may be used to identify whether there is a tumor in the breast of the subject, the size of the tumor, and the cancer may be identified at that time.

In specific embodiments, the subject may have a personal or family history of BC, has or has had breast anomaly, or is or was positive for mammography. The disclosed methods may be employed, for example, as a part of routine screening of the subject or may be employed upon indication that the subject has or is at risk for having BC or is in need of prognosis, response to treatment, recurrence survey, typing and/or staging of BC.

In cases where the subject has been identified as having BC, this condition may originate in the breast (tubular or globular or other) of the subject, or may be a primary cancer elsewhere in the subject that metastasizes in the breast. In some cases, when the subject is determined to have BC, the subject has BC in stage 0, 1, 2, 3, or 4.

The described methods and compositions may be used for screening for, diagnosing, or providing prognosis of any type of BC.

B. Screening Subjects

Screening of a subject may be performed as part of a regular checkup or physical examination. Therefore, in certain aspects the subject has not been diagnosed with cancer, and it is unknown whether the subject has a hyperproliferative disorder, such as a breast neoplasm. In other aspects, the subject is at risk of having BC, is suspected of having BC, or has a personal or family history of cancer, including BC. In some cases, the subject is known to have cancer and is screened as disclosed to determine the type of BC, staging of BC, treatment response to BC, and/or BC disease prognosis. In other cases, the subject has already been diagnosed for BC and may be subjected to surgery for BC resection and may undergo one or more of the disclosed methods to survey the recurrence of nodules or BC.

C. Diagnosing Subjects

Methods and compositions suitable for BC screening, diagnosis, and/or prognosis are provided. The methods include assaying 219 MRs of genomic DNA for determining the number of methylated nucleotides in each of these MRs, which may be referred to herein as "markers" or "biomarkers." The presence of methylated nucleotides in MRs is suggestive of potential BC.

The methylation of one or more MRs is suggestive of the BC presence in a subject or a potential for a subject to develop BC. The mSCORE can be used to determine the presence of cancerous lesions. If mSCORE=0 (in other words, if none of 219 MRs is methylated) then the subject does not have BC. If one or more of the MRs are methylated, the subject may develop BC or may already have BC. If particular additional conditions are satisfied, namely if mSCORE is greater than a specific threshold, the patient may be diagnosed with high accuracy as having or developing BC. A list of MRs is provided in Table 1. These MRs are target regions for the analysis described herein.

In specific embodiments, a subject is diagnosed as having BC. In specific embodiments, when a subject is diagnosed as having BC, the subject has BC stage 0, 1, 2, 3, or 4. In certain cases, following a positive diagnosis for BC, the subject is treated for BC. Treatment for BC may include surgery, chemotherapy, radiation, gene therapy or any treatment targeting the MRs, or a combination thereof. In specific embodiments, the chemotherapy modifies methylation level of all or some of the MRs. One can measure the effects in a consistent way by available technology (e.g., QPCR, MetSeq Next Generation Sequencing (NGS) sequencing, etc.).

The disclosed methods assist in accurate tumor diagnosis regardless of the stage of cancer, including the early stages (stages I and II) of BC in individuals. The methods of the disclosure allow an increase in the overall survival of BC patients by accurately diagnosing or detecting cancer at early stages and thereby they contribute significantly to reducing the cost of patients supported by health authorities.

The methylation of certain regions of genomic DNA has been discovered to be correlated with the presence or a high likelihood of developing BC. These regions of genomic DNA can also be used for determining the risk of developing BC, stage of BC, type of BC and/or monitoring of effects of treatment for BC. In other embodiments when none of 219 MRs is methylated, the absence of BC is confirmed.

Particular MRs are encompassed herein and disclosed in SEQ IDs NOs:1 to 219 in Table 1. The MRs are located on different chromosomes within the genome and are 51 nt in length. However, in some cases the region of the MR that is methylatable is shorter than 50 nt and/or the region of the MR that is informative for an aspect of BC is shorter than 50 nt. In certain embodiments, the region of the MR that is methylatable is combined with sequence that flanks the MR to be assayed and/or be informative. The methods of the disclosure may utilize all of the listed MRs for methylation level analysis or the methods may use less than all of the listed MRs for analysis.

In certain embodiments, the entirety of the MR is assayed for determining the number of methylated nucleotides, and thus the method(s) would assay the sequence of the one or more MRs of the disclosure. In some cases, the region of DNA that is assayed for methylation level includes some or all of the MRs, but also includes flanking sequence of the MR in the 5' direction, the 3' direction, or both. Such flanking regions extend up to but not including the first encountered CpG in the flanking region.

In certain embodiments for detecting the methylation level of one or more MRs, one can assay the MRs for sequence that is at least a part of the sequence of one or more of SEQ IDs NOs:1 to 219. In such cases, to determine methylation of an MR, one examines the methylation level of every C within the MR boundaries that is part of a CpG, irrespective whether the associated G is part of the MR.

In specific embodiments, the informative region within one or more of SEQ IDs NOs:1 to 219 is at least or no more than 1, 2, 3, . . . , 48, 49, or 50 nucleotides in length.

Table 1 provides exemplary MR utilized in methods and compositions of the disclosure. The MRs are extracted from the human genome sequence hg19. The genomic coordinates provided below correspond to the forward strand and are counted from the beginning of the chromosome.

D. Prognosis of Cancer

For prognosing BC, the methylation test of the defined MRs have to be taken at specific time intervals, e.g., before the treatment and after the treatment.

The response to treatment for BC, the prognosis of BC, or a combination thereof, and so forth can be determined by monitoring a change in methylation of specific MRs. For example, if some of the MRs of a subject's DNA (or nucleotides within specific MR) are found to be methylated before treatment and are found to be un-methylated after treatment, the response to treatment may be considered favorable and the prognosis is favorable (positive prognosis for positive outcome). Methylation of one or more of the MRs is suggestive of BC or the likelihood of developing BC. Absence of methylation of all 219 MRs indicates that there is no BC.

E. Treatment and Care

Subjects diagnosed with BC, or having prognosis of BC and their treatment outcome, may receive therapeutic treatment and care. The therapeutic treatment and care may be anti-cancer treatment and care, and specifically, anti-breast-cancer treatment and care. The therapeutic treatment and care may be the same as the treatment and care the subject may have received prior to diagnosis and/or prognosis, or different from the treatment and care that the subject may have received prior to diagnosis and/or prognosis.

Exemplary anti-cancer treatments include surgery, chemotherapy, radiation therapy, immunotherapy, gene therapy, targeted therapy, stem cell transplant, or combinations thereof. For example, chemotherapy may include a treatment with an effective amount of an anti-cancer agent. Exemplary anti-cancer agents include anthracyclines doxorubicin (Adriamycin®), pegylated liposomal doxorubicin (Doxil®), and epirubicin (Ellence®); taxanes paclitaxel (Taxol®) and docetaxel (Taxotere®); 5-fluorouracil (5-FU); cyclophosphamide (Cytoxan®); carboplatin (Paraplatin®); albumin-bound paclitaxel (Abraxane®); platinum agents (cisplatin, carboplatin); vinorelbine (Navelbine®); capecitabine (Xeloda®); gemcitabine (Gemzar®); ixabepilone (Ixempra®); eribulin (Halaven®), trastuzumab (Herceptin®), and combinations thereof.

Prognosis and selection of therapy may be influenced by the methylation level, mSCORE, and/or the following clinical and pathology features (based on conventional histology and immunohistochemistry) (Simpson et al., *J Clin Oncol*, 18(10): 2059-69, 2000): menopausal status of the patient; stage of the disease; grade of the primary tumor; Estrogen receptor (ER) and progesterone receptor (PR) status of the tumor; human epidermal growth factor type 2 receptor (HER2/neu) overexpression and/or amplification; histologic type; and the use of molecular profiling in breast cancer. This includes the following ER and PR status testing, HER2/neu receptor status testing, gene profile testing by microarray assay or reverse transcription-polymerase chain reaction (e.g., MammaPrint®, Oncotype® DX). On the basis of ER, PR, and HER2/neu results, breast cancer is classified as one of the following types: hormone receptor positive, HER2/neu positive, triple negative (ER, PR, and HER2/neu negative).

F. Exemplary Methylation Level and Score Quantification

Measuring the methylation level may be performed in a relative or absolute manner for each subject, marker and sample type (e.g., serum, urine, and so forth). The methylation level may be measured by any of the above-referenced exemplary methods. The results of such an exemplary measurement may be provided as a percent ranging from 0% (no methylation) to 100% (full methylation, in an absolute way). To compute the above-mentioned methylation score, the measurements provide the number of methylated nucleotides within individual MRs. In some cases, there is a specific value that can be compared to normal subjects (subjects that are cancer-free, for example in the same age range) values (in a relative way), for example.

In certain embodiments of the disclosure, a subject is assayed for a certain number of MRs to obtain methylation level for each MR. Then, in some cases, based on these figures, one can with a high accuracy diagnose the presence of BC.

For given MRs, a subject without BC should have no methylation of the considered MRs, while a subject who has these MRs methylated is prone to or already has BC.

V. Kits

Any of the compositions described herein may be part of a kit. In a non-limiting example, one or more reagents to determine methylation level of one or more MRs may be in the kit in suitable kit elements. The reagents may include primers, buffers, dinucleotides, labels, dyes, sequencing reagents, and/or microchips containing one or more nucleic acids, one or more PCR reagents, and so forth.

The kit may include primers that target one or more MRs described herein. This kit may be used in combination with any commercially available kit used for methylation quantification, such as QPCR SYBR® green Kit, QPCR-TaqMan® kit, QPCR HRM (high resolution melting) kit, QPCR FRET kit, emulsion PCR kit, high throughput library preparation kit, sequencing kit, hybridization kit for microarray or any software or script identifying the methylation of the MRs.

The kits can include a suitably aliquoted probes or primers. The components of the kits may be packaged either in aqueous media or in lyophilized form. However, the components of the kit may be provided as dried powder(s). When reagents and/or components are provided as a dry powder, the powder can be reconstituted by the addition of a suitable solvent. It is envisioned that the solvent may also be provided in another container means.

The kit may generally include at least one vial, test tube, flask, bottle, syringe, or other container means.

The kit may include devices suitable for extraction of a sample from an individual, including by non-invasive means. Such devices include swab (including rectal swab), phlebotomy material(s), scalpel, syringe, rod, and so forth.

The kit may include chips or microchips for detecting the methylation level of specific MRs. The kit may include chips or microchips for detecting the methylation level of all of the 219 MRs.

The kit may include any script or software for the analysis of the MRs described herein.

The present invention will be further understood by reference to the following non-limiting examples.

EXAMPLES

Example 1. The Biomarkers Diagnose Breast Cancer at High Sensitivity and 100% Specificity Materials and Methods Patients and Patient Samples. Samples were obtained from 50 individuals with BC. One cancerous and one non-cancerous (adjacent to the cancerous lesion) breast tissue samples were obtained from each patient. 25 patients had stage 1 BC, while the other 25 patients had stage 2 BC. Thus, both groups had an early stage BC.

Sample analysis. The samples were assayed through bisulfite sequencing using Illumina TrueSelect DNA capturing protocol followed by Illumina sequencing. The analysis was performed on the set of 219 MRs (defined SEQ ID NOS: 1-219 in Table 1). The methylation pattern of all 219 MRs was determined and the mSCORE for each patient calculated using Equation 1:

$$mSCORE = COV \times mTOT \qquad \text{Equation (1)}.$$

where mTOT, "total methylation", is the sum of methylated residues of all considered MRs for the patient; COV, "coverage" of a patient, is the number of MRs for the patient, which contain at least one methylated residue, and mSCORE, "methylation score" for a patient, is defined as a product of the patient's coverage and total methylation of 219 MRs.

Results

A summary of the results in presented in Table 2.

The results of the analysis revealed that the methylation level of the biomarkers provide a varying mSCORE for different patients. The methylation pattern of the 219 MRs differentiated between healthy controls and breast cancer patients with a 100% specificity and 94% sensitivity when the methylation score (mSCORE) calculated based on equation (1) has the threshold of 199, as can be seen from the fourth data row of Table 2. Table 2 shows how the sensitivity changes with the methylation score threshold, while always ensuring 100% specificity for every threshold value. Table 2 shows, as an illustration, the change of sensitivity while ensuring no false positive predictions.

TABLE 2

Sensitivity (%) in diagnosing breast cancer at 100% specificity using mSCORE values. Change of Sensitivity (%) with changes in the mSCORE value which is used as a decision threshold values. Specificity is also 100% (i.e., no false positives) is presented.

| mSCORE threshold | Sensitivity |
| --- | --- |
| mSCORE > 23 | Sensitivity = 100% |
| mSCORE > 34 | Sensitivity = 98% |
| mSCORE > 49 | Sensitivity = 96% |
| mSCORE > 199 | Sensitivity = 94% |
| mSCORE > 239 | Sensitivity = 92% |
| mSCORE > 274 | Sensitivity = 90% |
| mSCORE > 311 | Sensitivity = 88% |
| mSCORE > 329 | Sensitivity = 86% |
| mSCORE > 419 | Sensitivity = 84% |
| mSCORE > 447 | Sensitivity = 82% |
| mSCORE > 495 | Sensitivity = 80% |
| mSCORE > 503 | Sensitivity = 78% |
| mSCORE > 531 | Sensitivity = 76% |
| mSCORE > 702 | Sensitivity = 74% |
| mSCORE > 809 | Sensitivity = 72% |
| mSCORE > 923 | Sensitivity = 70% |
| mSCORE > 930 | Sensitivity = 68% |
| mSCORE > 1099 | Sensitivity = 66% |
| mSCORE > 1126 | Sensitivity = 64% |
| mSCORE > 1319 | Sensitivity = 62% |
| mSCORE > 1367 | Sensitivity = 60% |
| mSCORE > 1507 | Sensitivity = 58% |
| mSCORE > 2885 | Sensitivity = 56% |
| mSCORE > 3101 | Sensitivity = 54% |
| mSCORE > 3242 | Sensitivity = 52% |
| mSCORE > 3599 | Sensitivity = 50% |
| mSCORE > 3688 | Sensitivity = 48% |
| mSCORE > 3814 | Sensitivity = 46% |
| mSCORE > 4170 | Sensitivity = 44% |
| mSCORE > 4399 | Sensitivity = 42% |
| mSCORE > 5001 | Sensitivity = 40% |
| mSCORE > 5084 | Sensitivity = 38% |
| mSCORE > 5199 | Sensitivity = 36% |
| mSCORE > 5235 | Sensitivity = 34% |
| mSCORE > 5249 | Sensitivity = 32% |
| mSCORE > 5611 | Sensitivity = 30% |
| mSCORE > 5887 | Sensitivity = 28% |
| mSCORE > 6335 | Sensitivity = 26% |
| mSCORE > 6967 | Sensitivity = 24% |
| mSCORE > 7425 | Sensitivity = 22% |
| mSCORE > 13577 | Sensitivity = 20% |
| mSCORE > 16553 | Sensitivity = 18% |
| mSCORE > 17099 | Sensitivity = 16% |
| mSCORE > 17167 | Sensitivity = 14% |
| mSCORE > 19447 | Sensitivity = 12% |
| mSCORE > 20367 | Sensitivity = 10% |
| mSCORE > 21227 | Sensitivity = 8% |
| mSCORE > 24562 | Sensitivity = 6% |
| mSCORE > 37208 | Sensitivity = 4% |
| mSCORE > 39341 | Sensitivity = 2% |

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method of treating breast cancer in a human subject comprising: (a) detecting a methylation level in methylatable regions (MRs) of genomic DNA isolated a sample comprising genomic DNA obtained from the subject, wherein the MRs comprise SEQ IDs NOs: 1 to 219, wherein the sample is selected from the group consisting of breast tissue, blood, spittle, serum, plasma, urine, sputum, biopsy, and stool; and (ii) determining a methylation score (mSCORE), based on Equation 1:

$$mSCORE = COV \times mTOT \qquad \text{Equation (1),}$$

wherein COV is the number of MRs which contain at least one methylated residue and mTOT is the sum of methylated residues in the MRs, wherein the subject is diagnosed as having breast cancer if the methylation score within these 219 MRs as defined by equation (1) is between an mScore greater than 23 and about 274

(b) administering a breast cancer anticancer treatment to the subject.

2. The method of claim 1, wherein the sample is a breast tissue sample.

3. The method of claim 1, wherein:
(a) analyzing is by subjecting the isolated DNA to a methylation quantification assay
(b) the DNA methylation level is the number of methylated nucleotides in the MRs, the position of the methylated nucleotides in the MRs, or the percent of the methylated residues in the MRs; and/or
(c) the DNA methylation level in the subject is detected relative to the DNA methylation level in the same subject, in a different subject, or in a control subject not having cancer.

4. The method of claim 3, wherein the DNA methylation level is detected at the same level as that of the control subject, at a level below that of the control subject, or at a level above that of the control subject.

5. The method of claim 1, wherein the method of evaluating or diagnosing has a specificity of 100% and a sensitivity of at least 90% when the mSCORE across all 219 MRs is less than or equal to 274.

6. The method of claim 1, wherein the subject further undergoes one or more additional diagnostic assay(s).

7. The method of claim 6, wherein the one or more additional diagnostic assay(s) are selected from the group consisting of blood tests, mammography, non-invasive imaging, tissue biopsy, Her2 testing, hormone status testing, and combinations thereof.

8. The method of claim 1, further comprising administering an anticancer treatment to the subject selected from the group consisting of surgery, chemotherapy, radiation therapy, immunotherapy, gene therapy, and combinations thereof.

9. The method of claim 8, wherein the chemotherapy comprises a treatment with an effective amount of an anticancer agent selected from the group consisting of anthracyclines doxorubicin, pegylated liposomal doxorubicin, and epirubicin; taxanes paclitaxel and docetaxel; 5-fluorouracil (5-FU); cyclophosphamide; carboplatin; albumin-bound paclitaxel; platinum agents (cisplatin, carboplatin); vinorelbine; capecitabine; gemcitabine; ixabepilone; eribulin, trastuzumab, and combinations thereof.

10. The method of claim 1, wherein the subject has a personal history of breast cancer, including surgery for breast cancer; a family history of breast cancer; has breast cancer; and/or is positive for breast cancer genetic biomarkers selected from the group consisting of BRCA, ATM, P53, CHEK2, PTEN, CDH1, STK11, PALB2, and combinations thereof.

* * * * *

SEQUENCE LISTING

<160> NUMBER OF SEQ ID NOS: 219

<210> SEQ ID NO 1
<211> LENGTH: 51
<212> TYPE: DNA
<213> ORGANISM: Homo sapiens

<400> SEQUENCE: 1
ctaaaaatac aaaaaattag ccgggcgtgg tggcgcatgc ttgtaatccc a                 51

<210> SEQ ID NO 2
<211> LENGTH: 51
<212> TYPE: DNA
<213> ORGANISM: Homo sapiens

<400> SEQUENCE: 2
cgccgcgtct ccgcctgcct ccctgcgccg cgcgctctcc agtgccggct c                 51

<210> SEQ ID NO 3
<211> LENGTH: 51
<212> TYPE: DNA
<213> ORGANISM: Homo sapiens

<400> SEQUENCE: 3
ccgggaccgg gggcgggggc gggggcggac ggccgcgcgg agctgaggga c                 51

<210> SEQ ID NO 4
<211> LENGTH: 51
<212> TYPE: DNA
<213> ORGANISM: Homo sapiens

<400> SEQUENCE: 4
ggcctcgccg cgactccgcc gcccggaact cggggtcctt ggagaggctg c                 51

<210> SEQ ID NO 5
<211> LENGTH: 51
<212> TYPE: DNA
<213> ORGANISM: Homo sapiens

<400> SEQUENCE: 5
tggtttcgag ccgctcggga caggagggca agtgtaggcg atggggagg g                  51

<210> SEQ ID NO 6
<211> LENGTH: 51
<212> TYPE: DNA
<213> ORGANISM: Homo sapiens

<400> SEQUENCE: 6
cgtccctcgc gtagcgccac tcagccgccg gggccagagc gggagtcaag g                 51

<210> SEQ ID NO 7
<211> LENGTH: 51
<212> TYPE: DNA
<213> ORGANISM: Homo sapiens

<400> SEQUENCE: 7
acgcgttccc cgagctcccc gctttcgggg gtcggccccc tcggcggacg c                 51

<210> SEQ ID NO 8
<211> LENGTH: 51
<212> TYPE: DNA
<213> ORGANISM: Homo sapiens

```
<400> SEQUENCE: 8
tcgcgcgcgc ggggcggcgc ttccctctcg ccgcctaagg tcggaggcgc a          51

<210> SEQ ID NO 9
<211> LENGTH: 51
<212> TYPE: DNA
<213> ORGANISM: Homo sapiens

<400> SEQUENCE: 9
agcgctggaa actgggtgga cggcatgggt tggtctcagg atttgttccg c          51

<210> SEQ ID NO 10
<211> LENGTH: 51
<212> TYPE: DNA
<213> ORGANISM: Homo sapiens

<400> SEQUENCE: 10
gtccctgcgc gccttgatcc gggcggcggc taagggagag ccgagcacag a          51

<210> SEQ ID NO 11
<211> LENGTH: 51
<212> TYPE: DNA
<213> ORGANISM: Homo sapiens

<400> SEQUENCE: 11
agcgctctca cggaggacct gcgctgtcgc gcgaggggtc tgggagatgg g          51

<210> SEQ ID NO 12
<211> LENGTH: 51
<212> TYPE: DNA
<213> ORGANISM: Homo sapiens

<400> SEQUENCE: 12
cggctgggtt cgcgccgccg ccccggggcc cttggctcaa atttcacctc g          51

<210> SEQ ID NO 13
<211> LENGTH: 51
<212> TYPE: DNA
<213> ORGANISM: Homo sapiens

<400> SEQUENCE: 13
agaggctgcg gggggggggc ggcgggatga gctaggcgtc ggcggttgag t          51

<210> SEQ ID NO 14
<211> LENGTH: 51
<212> TYPE: DNA
<213> ORGANISM: Homo sapiens

<400> SEQUENCE: 14
tggtgctgtg gtcgagtgac cggtgagcgg gccggggtgg gatgcgctgt g          51

<210> SEQ ID NO 15
<211> LENGTH: 51
<212> TYPE: DNA
<213> ORGANISM: Homo sapiens

<400> SEQUENCE: 15
caaatatgcg gccaaagaat ccgcccgcgc ccggcgggcc tggcgcgtcc c          51

<210> SEQ ID NO 16
<211> LENGTH: 51
<212> TYPE: DNA
```

<213> ORGANISM: Homo sapiens

<400> SEQUENCE: 16
cgccttggac tggaagctgc acgggctgaa gtcggggtgc tcggccagcg t          51

<210> SEQ ID NO 17
<211> LENGTH: 51
<212> TYPE: DNA
<213> ORGANISM: Homo sapiens

<400> SEQUENCE: 17
tcgccgcctg ccggggaggc tggcccaggg tccccggcgc atagcggcca a          51

<210> SEQ ID NO 18
<211> LENGTH: 51
<212> TYPE: DNA
<213> ORGANISM: Homo sapiens

<400> SEQUENCE: 18
acgctcagct catccgcggc gtcggcgccc agcaggaacg agtccacgta g          51

<210> SEQ ID NO 19
<211> LENGTH: 51
<212> TYPE: DNA
<213> ORGANISM: Homo sapiens

<400> SEQUENCE: 19
ccgcccggcc cgacccacgg aaattatgaa actgcagatt tcatgtaaca a          51

<210> SEQ ID NO 20
<211> LENGTH: 51
<212> TYPE: DNA
<213> ORGANISM: Homo sapiens

<400> SEQUENCE: 20
gaataggaca aaaggcagat ttaggagaga cccagagtcc gtgagtcggg g          51

<210> SEQ ID NO 21
<211> LENGTH: 51
<212> TYPE: DNA
<213> ORGANISM: Homo sapiens

<400> SEQUENCE: 21
caccgcggcg gtggtgagga cacaggctgc ggtgtaagcc cgcgtcaccg c          51

<210> SEQ ID NO 22
<211> LENGTH: 51
<212> TYPE: DNA
<213> ORGANISM: Homo sapiens

<400> SEQUENCE: 22
gggtgggagc acacctgaag gggtactcga actcgacctc gatgctgagg t          51

<210> SEQ ID NO 23
<211> LENGTH: 51
<212> TYPE: DNA
<213> ORGANISM: Homo sapiens

<400> SEQUENCE: 23
tcgcgccgcc aatggcaagt tggagggaga gatgcaaata ccaggtgaga c          51

<210> SEQ ID NO 24
<211> LENGTH: 51

```
<212> TYPE: DNA
<213> ORGANISM: Homo sapiens

<400> SEQUENCE: 24
tgaaccctgc ttcctcgacc ccctgggag gccgccttct tcaggcgcct c        51

<210> SEQ ID NO 25
<211> LENGTH: 51
<212> TYPE: DNA
<213> ORGANISM: Homo sapiens

<400> SEQUENCE: 25
cggccgcctc ggggcgggag agaggccacc ggcagaccgt ccgcgtcctg c        51

<210> SEQ ID NO 26
<211> LENGTH: 51
<212> TYPE: DNA
<213> ORGANISM: Homo sapiens

<400> SEQUENCE: 26
tcggcctggg tgcccaccag cagcacaggc gcctgggggt tgtgcgtgcg g        51

<210> SEQ ID NO 27
<211> LENGTH: 51
<212> TYPE: DNA
<213> ORGANISM: Homo sapiens

<400> SEQUENCE: 27
ccctgggcgc cggacccagg catctccatt tagcaacctc ctggctgatg c        51

<210> SEQ ID NO 28
<211> LENGTH: 51
<212> TYPE: DNA
<213> ORGANISM: Homo sapiens

<400> SEQUENCE: 28
cttgggtccc cggtctgcga gggtcacacg gtcctcccgg acggcctctc c        51

<210> SEQ ID NO 29
<211> LENGTH: 51
<212> TYPE: DNA
<213> ORGANISM: Homo sapiens

<400> SEQUENCE: 29
cccaggaagc ccgggtccaa caccagctgc tggagccgcc tcagccgcac c        51

<210> SEQ ID NO 30
<211> LENGTH: 51
<212> TYPE: DNA
<213> ORGANISM: Homo sapiens

<400> SEQUENCE: 30
agggagcaac gtgcgtgtgt gtgcacatac actaattctg agacactgtg c        51

<210> SEQ ID NO 31
<211> LENGTH: 51
<212> TYPE: DNA
<213> ORGANISM: Homo sapiens

<400> SEQUENCE: 31
tccaatccac accgccgga gaccgcagct cgctccgacg cgcgcttcct g        51

<210> SEQ ID NO 32
```

<211> LENGTH: 51
<212> TYPE: DNA
<213> ORGANISM: Homo sapiens

<400> SEQUENCE: 32
gcgccgggcg ttcaaagcgc cgcggactca ctgccgaccg ttcaaatgca a    51

<210> SEQ ID NO 33
<211> LENGTH: 51
<212> TYPE: DNA
<213> ORGANISM: Homo sapiens

<400> SEQUENCE: 33
atccacaccc gccggagacc gcagctcgct ccgacgcgcg cttcctgcgc c    51

<210> SEQ ID NO 34
<211> LENGTH: 51
<212> TYPE: DNA
<213> ORGANISM: Homo sapiens

<400> SEQUENCE: 34
cgtcagcctt ccacccaccc caggggcg cgcgctcccc gcgcagcagc c    51

<210> SEQ ID NO 35
<211> LENGTH: 51
<212> TYPE: DNA
<213> ORGANISM: Homo sapiens

<400> SEQUENCE: 35
tccgcccgct ctctggcctc tcgtcctggc cgcgggaggt cacttcccgg g    51

<210> SEQ ID NO 36
<211> LENGTH: 51
<212> TYPE: DNA
<213> ORGANISM: Homo sapiens

<400> SEQUENCE: 36
tgggattaca ggtgtgagcc accgctcccg gccttgcaca ccatcttaag t    51

<210> SEQ ID NO 37
<211> LENGTH: 51
<212> TYPE: DNA
<213> ORGANISM: Homo sapiens

<400> SEQUENCE: 37
cttggccgcg gccgctgcgg ctgccgctgc gcgctcctgc ttgcgaaact t    51

<210> SEQ ID NO 38
<211> LENGTH: 51
<212> TYPE: DNA
<213> ORGANISM: Homo sapiens

<400> SEQUENCE: 38
gaggctgttt taccgcaggc gaagcacaat aacatgggaa tgaataaaat a    51

<210> SEQ ID NO 39
<211> LENGTH: 51
<212> TYPE: DNA
<213> ORGANISM: Homo sapiens

<400> SEQUENCE: 39
tgcgtctcgg tgagcttcag cgacgcggcc aggtctgcgc gctcgggccc g    51

<210> SEQ ID NO 40
<211> LENGTH: 51
<212> TYPE: DNA
<213> ORGANISM: Homo sapiens

<400> SEQUENCE: 40
ctccgacaga ggcgtctcca gtgaccacgt cctatttgtc tcaacacttg c            51

<210> SEQ ID NO 41
<211> LENGTH: 51
<212> TYPE: DNA
<213> ORGANISM: Homo sapiens

<400> SEQUENCE: 41
tctcctgctc ttccccacgg cgcccctctc cgttcgcgct tcctcccctc t            51

<210> SEQ ID NO 42
<211> LENGTH: 51
<212> TYPE: DNA
<213> ORGANISM: Homo sapiens

<400> SEQUENCE: 42
gatgcccccg aacatcgcgt tctaccccaa catcgcgatc cctccgaaca t            51

<210> SEQ ID NO 43
<211> LENGTH: 51
<212> TYPE: DNA
<213> ORGANISM: Homo sapiens

<400> SEQUENCE: 43
catcaagtaa actgaaacac tcaacaccgt ccacgcacgt cagtttactg g            51

<210> SEQ ID NO 44
<211> LENGTH: 51
<212> TYPE: DNA
<213> ORGANISM: Homo sapiens

<400> SEQUENCE: 44
ggatggtctc gatctcctga cctcgtgatc cgcccggaga tggcccctct t            51

<210> SEQ ID NO 45
<211> LENGTH: 51
<212> TYPE: DNA
<213> ORGANISM: Homo sapiens

<400> SEQUENCE: 45
gacccgcgaa ctttgccccc cacccctcgt ccccgctcca tactatcctt g            51

<210> SEQ ID NO 46
<211> LENGTH: 51
<212> TYPE: DNA
<213> ORGANISM: Homo sapiens

<400> SEQUENCE: 46
gccctcctaa aatgctggaa ttacaggctt gagccaccgc gcccggtcga t            51

<210> SEQ ID NO 47
<211> LENGTH: 51
<212> TYPE: DNA
<213> ORGANISM: Homo sapiens

<400> SEQUENCE: 47
gacggttcgc ccagggtggg cttcagccct ttcccagagt gctccgggcg t            51

```
<210> SEQ ID NO 48
<211> LENGTH: 51
<212> TYPE: DNA
<213> ORGANISM: Homo sapiens

<400> SEQUENCE: 48
ctgcgggcag cgctggccac gcggccccccg ccgccggcgg ttctccgtgg c        51

<210> SEQ ID NO 49
<211> LENGTH: 51
<212> TYPE: DNA
<213> ORGANISM: Homo sapiens

<400> SEQUENCE: 49
ttcgtagtcc atgccgggct tggagacggc gtcgaaggcg aaaacgcggc c        51

<210> SEQ ID NO 50
<211> LENGTH: 51
<212> TYPE: DNA
<213> ORGANISM: Homo sapiens

<400> SEQUENCE: 50
aggcccaggc gggaggatcg ctttagccca ggagtttgag aggaggctgg g        51

<210> SEQ ID NO 51
<211> LENGTH: 51
<212> TYPE: DNA
<213> ORGANISM: Homo sapiens

<400> SEQUENCE: 51
ggcaagaggc tcaaatatgc ggccaaagaa tccgcccgcg ccggcgggc c        51

<210> SEQ ID NO 52
<211> LENGTH: 51
<212> TYPE: DNA
<213> ORGANISM: Homo sapiens

<400> SEQUENCE: 52
ctcggccagc gtcgccgcct gccggggagg ctggcccagg gtccccggcg c        51

<210> SEQ ID NO 53
<211> LENGTH: 51
<212> TYPE: DNA
<213> ORGANISM: Homo sapiens

<400> SEQUENCE: 53
cagcgcctgg cccgcccggc ccgacccacg gaaattatga aactgcagat t        51

<210> SEQ ID NO 54
<211> LENGTH: 51
<212> TYPE: DNA
<213> ORGANISM: Homo sapiens

<400> SEQUENCE: 54
gttgccggcg cccgcgcccc cattggccgt gcgcgtcacg tgcccgtcca g        51

<210> SEQ ID NO 55
<211> LENGTH: 51
<212> TYPE: DNA
<213> ORGANISM: Homo sapiens

<400> SEQUENCE: 55
tcccgcgccc gacagcgccg gcagctctgg tctcctccgg agggctgctg t        51
```

<210> SEQ ID NO 56
<211> LENGTH: 51
<212> TYPE: DNA
<213> ORGANISM: Homo sapiens

<400> SEQUENCE: 56
gtggaaggcg cccgcgcccg cggtcgggta gcccagcgac gacgcgtacg g       51

<210> SEQ ID NO 57
<211> LENGTH: 51
<212> TYPE: DNA
<213> ORGANISM: Homo sapiens

<400> SEQUENCE: 57
gcgccgccgc cgcccgcccg ggaagacacg agcgcgcgcg cgtgcacaca t       51

<210> SEQ ID NO 58
<211> LENGTH: 51
<212> TYPE: DNA
<213> ORGANISM: Homo sapiens

<400> SEQUENCE: 58
agagcgccga gcgcggcgca gggactggag ttctcgccag cttcgggttc t       51

<210> SEQ ID NO 59
<211> LENGTH: 51
<212> TYPE: DNA
<213> ORGANISM: Homo sapiens

<400> SEQUENCE: 59
ccggcgccgg gcgcggccca ggcgacactc gcctcccaaa ctccagtctt c       51

<210> SEQ ID NO 60
<211> LENGTH: 51
<212> TYPE: DNA
<213> ORGANISM: Homo sapiens

<400> SEQUENCE: 60
cgcgcagcga agaagccgcc ccgcgggctg cggcgggcgg ggagcgccgc a       51

<210> SEQ ID NO 61
<211> LENGTH: 51
<212> TYPE: DNA
<213> ORGANISM: Homo sapiens

<400> SEQUENCE: 61
ctgcccgcgg tgcttctggc ccagtcttgc cacacggtca agccgcagtg g       51

<210> SEQ ID NO 62
<211> LENGTH: 51
<212> TYPE: DNA
<213> ORGANISM: Homo sapiens

<400> SEQUENCE: 62 tacctttca aaatgtcacc tctccccgcg gtgtgaccct cgaaagctag a        51

<210> SEQ ID NO 63
<211> LENGTH: 51
<212> TYPE: DNA
<213> ORGANISM: Homo sapiens

```
<400> SEQUENCE: 63
tatcactgtg gcatgatatc actgtggccg tccacctggg agccgattta t        51

<210> SEQ ID NO 64
<211> LENGTH: 51
<212> TYPE: DNA
<213> ORGANISM: Homo sapiens

<400> SEQUENCE: 64
ggatccggag gaaaatccgc aaactgggcc agctgtccct cagcgacgcc t        51

<210> SEQ ID NO 65
<211> LENGTH: 51
<212> TYPE: DNA
<213> ORGANISM: Homo sapiens

<400> SEQUENCE: 65
tggtgtccct tcgagggctc cgcgcgcctg gagccctcac acacctgctg g        51

<210> SEQ ID NO 66
<211> LENGTH: 51
<212> TYPE: DNA
<213> ORGANISM: Homo sapiens

<400> SEQUENCE: 66
ccgccctggc cgccgcctct tcccccagcc agtgcagtgc ggaaggccct g        51

<210> SEQ ID NO 67
<211> LENGTH: 51
<212> TYPE: DNA
<213> ORGANISM: Homo sapiens

<400> SEQUENCE: 67
tttggggagg gagcggcagg gcaacttttc tcggtccagg caggccgtgc a        51

<210> SEQ ID NO 68
<211> LENGTH: 51
<212> TYPE: DNA
<213> ORGANISM: Homo sapiens

<400> SEQUENCE: 68
cgtacatgga agcgggaacc cctactccgt ccatcccgcc gtaatggggc a        51

<210> SEQ ID NO 69
<211> LENGTH: 51
<212> TYPE: DNA
<213> ORGANISM: Homo sapiens

<400> SEQUENCE: 69
ggtggggagg ggaaaaaaac aaaaacgctg cggagcgttt tcgactttgc a        51

<210> SEQ ID NO 70
<211> LENGTH: 51
<212> TYPE: DNA
<213> ORGANISM: Homo sapiens

<400> SEQUENCE: 70
cttttcgaac cctgtagcgc tgttgcttcg cggtccatcg tcgccgctgc a        51

<210> SEQ ID NO 71
<211> LENGTH: 51
<212> TYPE: DNA
```

<213> ORGANISM: Homo sapiens

<400> SEQUENCE: 71
gcgacacctc ctccgcctcc gcctgcgctc gcggtggctc tcggcttcgc g            51

<210> SEQ ID NO 72
<211> LENGTH: 51
<212> TYPE: DNA
<213> ORGANISM: Homo sapiens

<400> SEQUENCE: 72
acgctccccg cagacagctg ggctcaggcc tggcgcgttg ggtgccgggg c            51

<210> SEQ ID NO 73
<211> LENGTH: 51
<212> TYPE: DNA
<213> ORGANISM: Homo sapiens

<400> SEQUENCE: 73
atgactagcg cgtaccctga cccccttccg caccaatatt tatatattta t            51

<210> SEQ ID NO 74
<211> LENGTH: 51
<212> TYPE: DNA
<213> ORGANISM: Homo sapiens

<400> SEQUENCE: 74
caggctctcc cgcctctccg ccgcgccgcg ccgcgccgcg cgtatttctg t            51

<210> SEQ ID NO 75
<211> LENGTH: 51
<212> TYPE: DNA
<213> ORGANISM: Homo sapiens

<400> SEQUENCE: 75
aacgcgccgc gtttcagcca gccggtctac gacgtgtatg tgactgaaaa c            51

<210> SEQ ID NO 76
<211> LENGTH: 51
<212> TYPE: DNA
<213> ORGANISM: Homo sapiens

<400> SEQUENCE: 76
cagcactttg ggaggccgac gcgggaggat cacttgaggt caggagttcg a            51

<210> SEQ ID NO 77
<211> LENGTH: 51
<212> TYPE: DNA
<213> ORGANISM: Homo sapiens

<400> SEQUENCE: 77
tatggccgat aaattgaaac gtcatcctag ttaaaagtaa cgtttttaac t            51

<210> SEQ ID NO 78
<211> LENGTH: 51
<212> TYPE: DNA
<213> ORGANISM: Homo sapiens

<400> SEQUENCE: 78
ggaggggcgg gtcaagggta cagggctgtg gggcggggcc ttggaggggc g            51

<210> SEQ ID NO 79
<211> LENGTH: 51

<212> TYPE: DNA
<213> ORGANISM: Homo sapiens

<400> SEQUENCE: 79
gcatccactt tcggaaggcc gggcctcgaa gggtgggcgc gcggggcagg a       51

<210> SEQ ID NO 80
<211> LENGTH: 51
<212> TYPE: DNA
<213> ORGANISM: Homo sapiens

<400> SEQUENCE: 80
cgcgagccgc aggacgcggg cgctgtgggt aacgaagttg ctcccggtgt g       51

<210> SEQ ID NO 81
<211> LENGTH: 51
<212> TYPE: DNA
<213> ORGANISM: Homo sapiens

<400> SEQUENCE: 81
cacggctgcg ggcgcgcgtg aacacacggc tgaaggtcat aggcagcgca t       51

<210> SEQ ID NO 82
<211> LENGTH: 51
<212> TYPE: DNA
<213> ORGANISM: Homo sapiens

<400> SEQUENCE: 82
gggaaagcgt gtgaaaccga ttccgtttat tgcccccagc ggcgggggag c       51

<210> SEQ ID NO 83
<211> LENGTH: 51
<212> TYPE: DNA
<213> ORGANISM: Homo sapiens

<400> SEQUENCE: 83
ccgcgtcccg ggctgcgcta ggcattccag cactgggccg cgcgcgtgat t       51

<210> SEQ ID NO 84
<211> LENGTH: 51
<212> TYPE: DNA
<213> ORGANISM: Homo sapiens

<400> SEQUENCE: 84 tcccccagg aagactcagc agctgtgccc agcacgagca tacggaatat g       51

<210> SEQ ID NO 85
<211> LENGTH: 51
<212> TYPE: DNA
<213> ORGANISM: Homo sapiens

<400> SEQUENCE: 85
ttacaggcct ggctgggcgc ggtgactcac gcctgtaatg ccagcactct g       51

<210> SEQ ID NO 86
<211> LENGTH: 51
<212> TYPE: DNA
<213> ORGANISM: Homo sapiens

<400> SEQUENCE: 86
aaggccgagg tgagacgctg gcacaccccg tcccgccgct tagccgcagg g       51

<210> SEQ ID NO 87

<210> SEQ ID NO 87
<211> LENGTH: 51
<212> TYPE: DNA
<213> ORGANISM: Homo sapiens

<400> SEQUENCE: 87
ctgcagaaca ccgccgggac ccggcacccg dacgcgcaag ggcgacaggg c    51

<210> SEQ ID NO 88
<211> LENGTH: 51
<212> TYPE: DNA
<213> ORGANISM: Homo sapiens

<400> SEQUENCE: 88
gcggaggagc tgcagcctcc aacaggttcg tagaacgcgc gctcgctccc t    51

<210> SEQ ID NO 89
<211> LENGTH: 51
<212> TYPE: DNA
<213> ORGANISM: Homo sapiens

<400> SEQUENCE: 89
ttaactgtct cacttgcccg ggccgccctc ccttctcccg cctgcgcgca c    51

<210> SEQ ID NO 90
<211> LENGTH: 51
<212> TYPE: DNA
<213> ORGANISM: Homo sapiens

<400> SEQUENCE: 90
aacggctcgc agctatccac cgaattaagc ctactataat ccccttcctt c    51

<210> SEQ ID NO 91
<211> LENGTH: 51
<212> TYPE: DNA
<213> ORGANISM: Homo sapiens

<400> SEQUENCE: 91
taatcacgtc tatttaaatt ctagcgcggt ccgccgcgct ctcaccggga a    51

<210> SEQ ID NO 92
<211> LENGTH: 51
<212> TYPE: DNA
<213> ORGANISM: Homo sapiens

<400> SEQUENCE: 92
tcatggtggc cgtggcgcac gtggccggct tccttctaga ggaccgcgcc g    51

<210> SEQ ID NO 93
<211> LENGTH: 51
<212> TYPE: DNA
<213> ORGANISM: Homo sapiens

<400> SEQUENCE: 93
acccgcggag gcaggacccg aggctcttcc gacctgcata ctcagtaaga t    51

<210> SEQ ID NO 94
<211> LENGTH: 51
<212> TYPE: DNA
<213> ORGANISM: Homo sapiens

<400> SEQUENCE: 94
ggcacaatgt ccgggctgtg ggaacgcgct cgccctcatt agcatcccgg g    51

<210> SEQ ID NO 95
<211> LENGTH: 51
<212> TYPE: DNA
<213> ORGANISM: Homo sapiens

<400> SEQUENCE: 95
ggctgacacc aggagtgagc agaacgaggg gggagagcga atgaggaggc a         51

<210> SEQ ID NO 96
<211> LENGTH: 51
<212> TYPE: DNA
<213> ORGANISM: Homo sapiens

<400> SEQUENCE: 96
aggacggggc cggggccggg agagggcggg gagggcgctc ctgggaggtc a         51

<210> SEQ ID NO 97
<211> LENGTH: 51
<212> TYPE: DNA
<213> ORGANISM: Homo sapiens

<400> SEQUENCE: 97
actaccgggc tcaggggcgc gcggtgccgg cccctgctgt ccccgaagaa g         51

<210> SEQ ID NO 98
<211> LENGTH: 51
<212> TYPE: DNA
<213> ORGANISM: Homo sapiens

<400> SEQUENCE: 98
cccaggacct tgtgggctgg gcaggtaaga agcgccggcg gccaccagct g         51

<210> SEQ ID NO 99
<211> LENGTH: 51
<212> TYPE: DNA
<213> ORGANISM: Homo sapiens

<400> SEQUENCE: 99
tattattatt attattatta acagcaaaca ttaaatcacg ttttctccga a         51

<210> SEQ ID NO 100
<211> LENGTH: 51
<212> TYPE: DNA
<213> ORGANISM: Homo sapiens

<400> SEQUENCE: 100
cagggaccag gagggctcgg cggggccacc accccgcgt gcacagtgga g          51

<210> SEQ ID NO 101
<211> LENGTH: 51
<212> TYPE: DNA
<213> ORGANISM: Homo sapiens

<400> SEQUENCE: 101
cggtggcggc agccccgcgc ccaggccgag cagagtcagg gctgccagcg c         51

<210> SEQ ID NO 102
<211> LENGTH: 51
<212> TYPE: DNA
<213> ORGANISM: Homo sapiens

<400> SEQUENCE: 102
acgcccagcc gcgcctgcga gccgtaaggg tcggtaagca tgtaggcgga t         51

```
<210> SEQ ID NO 103
<211> LENGTH: 51
<212> TYPE: DNA
<213> ORGANISM: Homo sapiens

<400> SEQUENCE: 103
tcgcagcgcc gaagccacga gcaccagcac cgcggccacc aatgccagcc g          51

<210> SEQ ID NO 104
<211> LENGTH: 51
<212> TYPE: DNA
<213> ORGANISM: Homo sapiens

<400> SEQUENCE: 104
actttgggag gcccaggcgg gaggatcgct ttagcccagg agtttgagag g          51

<210> SEQ ID NO 105
<211> LENGTH: 51
<212> TYPE: DNA
<213> ORGANISM: Homo sapiens

<400> SEQUENCE: 105
cgcgcagcca gccggcaccc gcgtgcgtgt ccttgaggcg gaagaggcgg c          51

<210> SEQ ID NO 106
<211> LENGTH: 51
<212> TYPE: DNA
<213> ORGANISM: Homo sapiens

<400> SEQUENCE: 106
ccgcgccttg tggagatcgc tgtcaaggga agtgaaggag cacgtgggca c          51

<210> SEQ ID NO 107
<211> LENGTH: 51
<212> TYPE: DNA
<213> ORGANISM: Homo sapiens

<400> SEQUENCE: 107
gggcgcttgt gttgtgtgcg cgcaccaaag ctggtagtgg ggaatgggaa c          51

<210> SEQ ID NO 108
<211> LENGTH: 51
<212> TYPE: DNA
<213> ORGANISM: Homo sapiens

<400> SEQUENCE: 108
ataaagcgtg aagagggatc gctgggtagc tgagcgccgc cggcggccgc c          51

<210> SEQ ID NO 109
<211> LENGTH: 51
<212> TYPE: DNA
<213> ORGANISM: Homo sapiens

<400> SEQUENCE: 109
gccgcgcgct gggaggttaa tagcgactga cgacaaaggg ccaaggtgca a          51

<210> SEQ ID NO 110
<211> LENGTH: 51
<212> TYPE: DNA
<213> ORGANISM: Homo sapiens

<400> SEQUENCE: 110
tggtctggaa cttctgacct caggtgatcc gtccgcctcg gccttccaaa a          51
```

<210> SEQ ID NO 111
<211> LENGTH: 51
<212> TYPE: DNA
<213> ORGANISM: Homo sapiens

<400> SEQUENCE: 111
tccaggcagg tgccgaggtg ccgaggttcc gagcaggttc ctgtctggaa t       51

<210> SEQ ID NO 112
<211> LENGTH: 51
<212> TYPE: DNA
<213> ORGANISM: Homo sapiens

<400> SEQUENCE: 112
ggccccggct cggcgcgccg atgccccgcg gcgtcctctc cccgggcgcc g       51

<210> SEQ ID NO 113
<211> LENGTH: 51
<212> TYPE: DNA
<213> ORGANISM: Homo sapiens

<400> SEQUENCE: 113
ttcatgttcc gtagcgttgc ggcctcgtgg ccgggcagct ggaagcgcag g       51

<210> SEQ ID NO 114
<211> LENGTH: 51
<212> TYPE: DNA
<213> ORGANISM: Homo sapiens

<400> SEQUENCE: 114
tgcgcggctg cagccggcgg atccctcttc ccaggctccg tggtcgcgca g       51

<210> SEQ ID NO 115
<211> LENGTH: 51
<212> TYPE: DNA
<213> ORGANISM: Homo sapiens

<400> SEQUENCE: 115
ggaaaaccgg agcaggtatg gaggccgcag cccagaaggt agcagtgggg c       51

<210> SEQ ID NO 116
<211> LENGTH: 51
<212> TYPE: DNA
<213> ORGANISM: Homo sapiens

<400> SEQUENCE: 116
tcatgcgagg gtcccccgtc tctgctcctg gccctgccac gagccagttg g       51

<210> SEQ ID NO 117
<211> LENGTH: 51
<212> TYPE: DNA
<213> ORGANISM: Homo sapiens

<400> SEQUENCE: 117
tcaggggcgc gcggtgccgg ccctgctgt ccccgaagaa ggacatttct g        51

<210> SEQ ID NO 118
<211> LENGTH: 51
<212> TYPE: DNA

<400> SEQUENCE: 118
gcggtgtgac cctcgaaagc tagacgtgcc caggaggcag cagcccaggc c          51

<210> SEQ ID NO 119
<211> LENGTH: 51
<212> TYPE: DNA
<213> ORGANISM: Homo sapiens

<400> SEQUENCE: 119
cgtgagccac cgtgcccggc ctatttccca acttctgaaa aatgtgtgca c          51

<210> SEQ ID NO 120
<211> LENGTH: 51
<212> TYPE: DNA
<213> ORGANISM: Homo sapiens

<400> SEQUENCE: 120
gctggcacac cccgtcccgc cgcttagccg cagggcctcc cctctgacct g          51

<210> SEQ ID NO 121
<211> LENGTH: 51
<212> TYPE: DNA
<213> ORGANISM: Homo sapiens

<400> SEQUENCE: 121
gggcgggcgc cgctgagcgc gtctaggtgg ccgcaggtcg cggcatcgcg t          51

<210> SEQ ID NO 122
<211> LENGTH: 51
<212> TYPE: DNA
<213> ORGANISM: Homo sapiens

<400> SEQUENCE: 122
cagcgggtgg aggttcgggg ctgggtggat tatgagctga aggcagggcc g          51

<210> SEQ ID NO 123
<211> LENGTH: 51
<212> TYPE: DNA
<213> ORGANISM: Homo sapiens

<400> SEQUENCE: 123
gcagcttcat gccacagcac tgagtccgcc cgcctgccgg tgtccacact g          51

<210> SEQ ID NO 124
<211> LENGTH: 51
<212> TYPE: DNA
<213> ORGANISM: Homo sapiens

<400> SEQUENCE: 124
ctctccagct gggcagcagc ttcatgccac agcactgagt ccgcccgcct g          51

<210> SEQ ID NO 125
<211> LENGTH: 51
<212> TYPE: DNA
<213> ORGANISM: Homo sapiens

<400> SEQUENCE: 125
ctggcttcct ctcggtgcac ggcaggctct gctccccggg ggccaggagg c          51

<210> SEQ ID NO 126
<211> LENGTH: 51
<212> TYPE: DNA

<213> ORGANISM: Homo sapiens

<400> SEQUENCE: 126
ccagcagccc gtcggacgcg gtcaggacgc cgccgtagcc gccgccgtag g    51

<210> SEQ ID NO 127
<211> LENGTH: 51
<212> TYPE: DNA
<213> ORGANISM: Homo sapiens

<400> SEQUENCE: 127
gcccaaaacg cacggagccg ccgcccaggc ctccgaagga cgacgtggcc g    51

<210> SEQ ID NO 128
<211> LENGTH: 51
<212> TYPE: DNA
<213> ORGANISM: Homo sapiens

<400> SEQUENCE: 128
tcggacgcgg tcaggacgcc gccgtagccg ccgccgtagg cccccgagga g    51

<210> SEQ ID NO 129
<211> LENGTH: 51
<212> TYPE: DNA
<213> ORGANISM: Homo sapiens

<400> SEQUENCE: 129
acggagccgc cgcccaggcc tccgaaggac gacgtggccg acgactggcg a    51

<210> SEQ ID NO 130
<211> LENGTH: 51
<212> TYPE: DNA
<213> ORGANISM: Homo sapiens

<400> SEQUENCE: 130
ccgccagccc ggcccgctcc gcctcggctg ggcggccggg ttggcacaag c    51

<210> SEQ ID NO 131
<211> LENGTH: 51
<212> TYPE: DNA
<213> ORGANISM: Homo sapiens

<400> SEQUENCE: 131
acctgtgcac gctgtagggg cccgggacgg ctcagcacca tcacctgcac c    51

<210> SEQ ID NO 132
<211> LENGTH: 51
<212> TYPE: DNA
<213> ORGANISM: Homo sapiens

<400> SEQUENCE: 132
tccccgaagc cgagccgctc cccgcctccc accctagcc gaggcgctcc t    51

<210> SEQ ID NO 133
<211> LENGTH: 51
<212> TYPE: DNA
<213> ORGANISM: Homo sapiens

<400> SEQUENCE: 133
ccagagcccg gtcagggcga gggggcggag gcttcgaggc cttccgggct g    51

<210> SEQ ID NO 134
<211> LENGTH: 51

```
<212> TYPE: DNA
<213> ORGANISM: Homo sapiens

<400> SEQUENCE: 134
agacggtggg acaggcgccc gctgcgcccc gcttgccctt aaagcagagg t          51

<210> SEQ ID NO 135
<211> LENGTH: 51
<212> TYPE: DNA
<213> ORGANISM: Homo sapiens

<400> SEQUENCE: 135
gcgcgctcgc gccggagcag cgctgccgcc gcgcggggt cgatcgcagg c           51

<210> SEQ ID NO 136
<211> LENGTH: 51
<212> TYPE: DNA
<213> ORGANISM: Homo sapiens

<400> SEQUENCE: 136
ccaggcgggc gagggctgga caggagaggg tgtgggcgca ggcctctggg c          51

<210> SEQ ID NO 137
<211> LENGTH: 51
<212> TYPE: DNA
<213> ORGANISM: Homo sapiens

<400> SEQUENCE: 137
cgcgggagga tcacttgagg tcaggagttc gagaccagcc tggccaatat g          51

<210> SEQ ID NO 138
<211> LENGTH: 51
<212> TYPE: DNA
<213> ORGANISM: Homo sapiens

<400> SEQUENCE: 138
tcggcgtgac cacctttggc gcgtcccgcc accactccgc gggcgacgtg g          51

<210> SEQ ID NO 139
<211> LENGTH: 51
<212> TYPE: DNA
<213> ORGANISM: Homo sapiens

<400> SEQUENCE: 139
atcccgggga ggtgcaggaa gacagcgagc tcgaggcagt ggggtgcgac t          51

<210> SEQ ID NO 140
<211> LENGTH: 51
<212> TYPE: DNA
<213> ORGANISM: Homo sapiens

<400> SEQUENCE: 140
gcccaccaca caccgagccc atccagggac acccgaactt cacattaaac a          51

<210> SEQ ID NO 141
<211> LENGTH: 51
<212> TYPE: DNA
<213> ORGANISM: Homo sapiens

<400> SEQUENCE: 141
cgtcactcag ccggccgccc agggagctcc tgggcccggc ccgggagagg g          51

<210> SEQ ID NO 142
```

<210> SEQ ID NO 142
<211> LENGTH: 51
<212> TYPE: DNA
<213> ORGANISM: Homo sapiens

<400> SEQUENCE: 142
ccccttgcaa cgctaggatt cgttattgat agtggtgagc gctgggaatg a        51

<210> SEQ ID NO 143
<211> LENGTH: 51
<212> TYPE: DNA
<213> ORGANISM: Homo sapiens

<400> SEQUENCE: 143
ttatcttcag gctgcagatg tccggatagg aaactccggc aggagatccg a        51

<210> SEQ ID NO 144
<211> LENGTH: 51
<212> TYPE: DNA
<213> ORGANISM: Homo sapiens

<400> SEQUENCE: 144
gacagatcca gaacgccgtc tacgcctacc ggcggcagat cttcaagccc g        51

<210> SEQ ID NO 145
<211> LENGTH: 51
<212> TYPE: DNA
<213> ORGANISM: Homo sapiens

<400> SEQUENCE: 145
tcgcgctggc agcgctcgcc tggctttgca gagcttttag agttacccac c        51

<210> SEQ ID NO 146
<211> LENGTH: 51
<212> TYPE: DNA
<213> ORGANISM: Homo sapiens

<400> SEQUENCE: 146
agacgctttc gtgcaggagg gacgacgact cccctcacgc cttcgtggcc c        51

<210> SEQ ID NO 147
<211> LENGTH: 51
<212> TYPE: DNA
<213> ORGANISM: Homo sapiens

<400> SEQUENCE: 147
caggttaatt tttcccgcga cgcgcttcgt atcgcttctt acaccaaata t        51

<210> SEQ ID NO 148
<211> LENGTH: 51
<212> TYPE: DNA
<213> ORGANISM: Homo sapiens

<400> SEQUENCE: 148
cggggcctcc cagcggcttc ccggagctcc tggagcccca atcccattcc c        51

<210> SEQ ID NO 149
<211> LENGTH: 51
<212> TYPE: DNA
<213> ORGANISM: Homo sapiens

<400> SEQUENCE: 149
cggagtccgc ctcgcatcca gcagcgaaga catgttccgg tccggggtct c        51

```
<210> SEQ ID NO 150
<211> LENGTH: 51
<212> TYPE: DNA
<213> ORGANISM: Homo sapiens

<400> SEQUENCE: 150
cacagtccag ggggagccgg caggcggcct cctccccgag ccggaggagc t          51

<210> SEQ ID NO 151
<211> LENGTH: 51
<212> TYPE: DNA
<213> ORGANISM: Homo sapiens

<400> SEQUENCE: 151
cgccagcccg agctactccg cgctggacaa gacgccccac tgttctgggg c          51

<210> SEQ ID NO 152
<211> LENGTH: 51
<212> TYPE: DNA
<213> ORGANISM: Homo sapiens

<400> SEQUENCE: 152
tgcagcccag cgcgcgcgag acgacccaag acccacgcgc actcgcacga g          51

<210> SEQ ID NO 153
<211> LENGTH: 51
<212> TYPE: DNA
<213> ORGANISM: Homo sapiens

<400> SEQUENCE: 153
gccagtgact gcacgcgctg acgcgcctcg cgctcgaagg ccgccttgtc c          51

<210> SEQ ID NO 154
<211> LENGTH: 51
<212> TYPE: DNA
<213> ORGANISM: Homo sapiens

<400> SEQUENCE: 154
acggcgcagc gcagatgcag cccatgcacc gctacgacgt gagcgccctg c          51

<210> SEQ ID NO 155
<211> LENGTH: 51
<212> TYPE: DNA
<213> ORGANISM: Homo sapiens

<400> SEQUENCE: 155
agagccgacg cgcgggcaaa ttgaggccga gctgacgagc tccggcgggt g          51

<210> SEQ ID NO 156
<211> LENGTH: 51
<212> TYPE: DNA
<213> ORGANISM: Homo sapiens

<400> SEQUENCE: 156
cgcctcactc cggcggataa tgagataaag tgtcagagac acggcgagaa c          51

<210> SEQ ID NO 157
<211> LENGTH: 51
<212> TYPE: DNA
<213> ORGANISM: Homo sapiens

<400> SEQUENCE: 157
cgcgctcttc gcgggacggc agagggaggg tctctgaggc gcgtggaatc a          51
```

<210> SEQ ID NO 158
<211> LENGTH: 51
<212> TYPE: DNA
<213> ORGANISM: Homo sapiens

<400> SEQUENCE: 158
acgcgtcgac tctggcgccg ctgccggcgc cgctggcggt ggctgtacca g          51

<210> SEQ ID NO 159
<211> LENGTH: 51
<212> TYPE: DNA
<213> ORGANISM: Homo sapiens

<400> SEQUENCE: 159
gcgcgcagag aggcagcttc aggccagggg agtgcaaggt cacagaggtc a          51

<210> SEQ ID NO 160
<211> LENGTH: 51
<212> TYPE: DNA
<213> ORGANISM: Homo sapiens

<400> SEQUENCE: 160
gccagctcgc gctccgtcga gttcttcctg tcgcgccggc gccgggcgcg c          51

<210> SEQ ID NO 161
<211> LENGTH: 51
<212> TYPE: DNA
<213> ORGANISM: Homo sapiens

<400> SEQUENCE: 161
ctccctcccg cggacctgca ggaagcaggc tgtttccttt cagtctcctc c          51

<210> SEQ ID NO 162
<211> LENGTH: 51
<212> TYPE: DNA
<213> ORGANISM: Homo sapiens

<400> SEQUENCE: 162
cgggaggacg cactttccag atgtggggat gtgtgtgcct gtctcaaccc c          51

<210> SEQ ID NO 163
<211> LENGTH: 51
<212> TYPE: DNA
<213> ORGANISM: Homo sapiens

<400> SEQUENCE: 163
gccgaggagc gcgcgctgcg ccgcccgggc cacctctacc tgctgcaccg c          51

<210> SEQ ID NO 164
<211> LENGTH: 51
<212> TYPE: DNA
<213> ORGANISM: Homo sapiens

<400> SEQUENCE: 164
aggccccgcc ctctccccga agctgtgtgc ggcactggcc aggtggactg g          51

<210> SEQ ID NO 165
<211> LENGTH: 51
<212> TYPE: DNA
<213> ORGANISM: Homo sapiens

<400> SEQUENCE: 165
cctcactccg gcggataatg agataaagtg tcagagacac ggcgagaaca a          51

<210> SEQ ID NO 166
<211> LENGTH: 51
<212> TYPE: DNA
<213> ORGANISM: Homo sapiens

<400> SEQUENCE: 166
tccaacacca gctgctggag ccgcctcagc cgcacctcgg ctgacatgtt g         51

<210> SEQ ID NO 167
<211> LENGTH: 51
<212> TYPE: DNA
<213> ORGANISM: Homo sapiens

<400> SEQUENCE: 167
cggcgccggg ccctgcccag gcgggcgagg gctggacagg agagggtgtg g         51

<210> SEQ ID NO 168
<211> LENGTH: 51
<212> TYPE: DNA
<213> ORGANISM: Homo sapiens

<400> SEQUENCE: 168
tacccagggc gaggccagct tccaggaggt cagcgccaac accgccggca g         51

<210> SEQ ID NO 169
<211> LENGTH: 51
<212> TYPE: DNA
<213> ORGANISM: Homo sapiens

<400> SEQUENCE: 169
ggtgcggcac cgctggccca ggcccgggcg cggctggaca tggccaccta c         51

<210> SEQ ID NO 170
<211> LENGTH: 51
<212> TYPE: DNA
<213> ORGANISM: Homo sapiens

<400> SEQUENCE: 170
cagggcccga aacgcgccca tcgccccgtg ctgtgccatg ctcgggtttc a         51

<210> SEQ ID NO 171
<211> LENGTH: 51
<212> TYPE: DNA
<213> ORGANISM: Homo sapiens

<400> SEQUENCE: 171
agggttgaga ggagaaggga aagacagaca cagacgcgcc gggccggtgg a         51

<210> SEQ ID NO 172
<211> LENGTH: 51
<212> TYPE: DNA
<213> ORGANISM: Homo sapiens

<400> SEQUENCE: 172
ttgaatatgc tgcaaaacat ccacagagcc tcaaagcgag ctcggaacct g         51

<210> SEQ ID NO 173
<211> LENGTH: 51
<212> TYPE: DNA
<213> ORGANISM: Homo sapiens -continued

<400> SEQUENCE: 173
attcaaattg ccactttaaa aaacatagaa cacgagaata gaataccgac t       51

<210> SEQ ID NO 174
<211> LENGTH: 51
<212> TYPE: DNA
<213> ORGANISM: Homo sapiens

<400> SEQUENCE: 174
ggcgcccgtc ctacccggag ccaagtgccc gacgcgcgcg caccgcacgc c       51

<210> SEQ ID NO 175
<211> LENGTH: 51
<212> TYPE: DNA
<213> ORGANISM: Homo sapiens

<400> SEQUENCE: 175
gccgccgcgc tcttagtgag cagcctgcgg aggcacagcg cgccggaacc g       51

<210> SEQ ID NO 176
<211> LENGTH: 51
<212> TYPE: DNA
<213> ORGANISM: Homo sapiens

<400> SEQUENCE: 176
ccgcggtgct tctggcccag tcttgccaca cggtcaagcc gcagtggtgg c       51

<210> SEQ ID NO 177
<211> LENGTH: 51
<212> TYPE: DNA
<213> ORGANISM: Homo sapiens

<400> SEQUENCE: 177
gcccggacct ggcgcgtgcg ctgggggagc tccaccggcc ggagctgcgg c       51

<210> SEQ ID NO 178
<211> LENGTH: 51
<212> TYPE: DNA
<213> ORGANISM: Homo sapiens

<400> SEQUENCE: 178
cttgacgcgt ccgggcgcct ccgcggtgag tcgcgccgcc gctctcgggg t       51

<210> SEQ ID NO 179
<211> LENGTH: 51
<212> TYPE: DNA
<213> ORGANISM: Homo sapiens

<400> SEQUENCE: 179
ctcgccaggc cacgtcgcgg ttggtggtcg gagagggcga ggggtcccag g       51

<210> SEQ ID NO 180
<211> LENGTH: 51
<212> TYPE: DNA
<213> ORGANISM: Homo sapiens

<400> SEQUENCE: 180
ttctccggta ggaccccggg gtggattcgc gcgtccgcgg cgaggctaga g       51

<210> SEQ ID NO 181
<211> LENGTH: 51
<212> TYPE: DNA

<213> ORGANISM: Homo sapiens

<400> SEQUENCE: 181
cgcggcacaa tgtccgggct gtgggaacgc gctcgccctc attagcatcc c    51

<210> SEQ ID NO 182
<211> LENGTH: 51
<212> TYPE: DNA
<213> ORGANISM: Homo sapiens

<400> SEQUENCE: 182
atgacttcgc tgttgtcacc gagcgccccg cccaccgcgt tctccgaccc g    51

<210> SEQ ID NO 183
<211> LENGTH: 51
<212> TYPE: DNA
<213> ORGANISM: Homo sapiens

<400> SEQUENCE: 183
acgggccgaa gcgggccttc cggccggggt tggggataaa gtgccccgga g    51

<210> SEQ ID NO 184
<211> LENGTH: 51
<212> TYPE: DNA
<213> ORGANISM: Homo sapiens

<400> SEQUENCE: 184
tccttccatt ttctgcctcg ccttccccct accccgcgtt tctctgcctc a    51

<210> SEQ ID NO 185
<211> LENGTH: 51
<212> TYPE: DNA
<213> ORGANISM: Homo sapiens

<400> SEQUENCE: 185
atccgcgccg cgcctcgctc ccgcccccgt gactcgaggc gcagcgtgcg t    51

<210> SEQ ID NO 186
<211> LENGTH: 51
<212> TYPE: DNA
<213> ORGANISM: Homo sapiens

<400> SEQUENCE: 186
gcgcagcgcc cgctcggcca cggcaggggg cggccgcgcg cgacccagcc a    51

<210> SEQ ID NO 187
<211> LENGTH: 51
<212> TYPE: DNA
<213> ORGANISM: Homo sapiens

<400> SEQUENCE: 187
catgttccgt agcgttgcgg cctcgtggcc gggcagctgg aagcgcagga c    51

<210> SEQ ID NO 188
<211> LENGTH: 51
<212> TYPE: DNA
<213> ORGANISM: Homo sapiens

<400> SEQUENCE: 188
gagacgctgg ggctccggaa agagacgagc ccagtagaaa gcgcgcagag a    51

<210> SEQ ID NO 189
<211> LENGTH: 51

<212> TYPE: DNA
<213> ORGANISM: Homo sapiens

<400> SEQUENCE: 189
ctccccgaag ctgtgtgcgg cactggccag gtggactggg gccatggctg g        51

<210> SEQ ID NO 190
<211> LENGTH: 51
<212> TYPE: DNA
<213> ORGANISM: Homo sapiens

<400> SEQUENCE: 190
cccccgtatc cccagccctt ggcaacactg gagtgcacac gccgccacgg t        51

<210> SEQ ID NO 191
<211> LENGTH: 51
<212> TYPE: DNA
<213> ORGANISM: Homo sapiens

<400> SEQUENCE: 191
gggcgagagg cgcgagcaca caagcgagta gagacaccga gaacgaacga g        51

<210> SEQ ID NO 192
<211> LENGTH: 51
<212> TYPE: DNA
<213> ORGANISM: Homo sapiens

<400> SEQUENCE: 192
gcgcgtggga ggcgagatcc cgccagttac aacacgagtt cggtccccaa t        51

<210> SEQ ID NO 193
<211> LENGTH: 51
<212> TYPE: DNA
<213> ORGANISM: Homo sapiens

<400> SEQUENCE: 193
cacggcctcg ccctgggcgc ggggcatcac cggcgcggag gcccgagggc g        51

<210> SEQ ID NO 194
<211> LENGTH: 51
<212> TYPE: DNA
<213> ORGANISM: Homo sapiens

<400> SEQUENCE: 194
gcttcctgga gagatacatc tacaaccggg aggagttcgc gcgcttcgac a        51

<210> SEQ ID NO 195
<211> LENGTH: 51
<212> TYPE: DNA
<213> ORGANISM: Homo sapiens

<400> SEQUENCE: 195
agcgacgtgg gggagttccg ggcggtgacg gagctggggc ggcctgctgc g        51

<210> SEQ ID NO 196
<211> LENGTH: 51
<212> TYPE: DNA
<213> ORGANISM: Homo sapiens

<400> SEQUENCE: 196
atgcgagggt ccccgtctc tgctcctggc cctgccacga gccagttggc t         51

<210> SEQ ID NO 197

<211> LENGTH: 51
<212> TYPE: DNA
<213> ORGANISM: Homo sapiens

<400> SEQUENCE: 197
tgcccggggg agcgcagggc gggagctgct gagcaggcgg agggagggcg g            51

<210> SEQ ID NO 198
<211> LENGTH: 51
<212> TYPE: DNA
<213> ORGANISM: Homo sapiens

<400> SEQUENCE: 198
actgcctccg gaccacatcg ggcttcgctg cgctgagccc cagtcgccaa c            51

<210> SEQ ID NO 199
<211> LENGTH: 51
<212> TYPE: DNA
<213> ORGANISM: Homo sapiens

<400> SEQUENCE: 199
tcacaaacac agctgaccgt ctcacagctg cacacctgca ccgctcacga g            51

<210> SEQ ID NO 200
<211> LENGTH: 51
<212> TYPE: DNA
<213> ORGANISM: Homo sapiens

<400> SEQUENCE: 200
tttaagtttt cccacgagca aggcagcgaa aatagaatgt ggtagataga a            51

<210> SEQ ID NO 201
<211> LENGTH: 51
<212> TYPE: DNA
<213> ORGANISM: Homo sapiens

<400> SEQUENCE: 201
gccttacact ctatgattgc tcctaccgac tcccatgagg aagtgcgatc g            51

<210> SEQ ID NO 202
<211> LENGTH: 51
<212> TYPE: DNA
<213> ORGANISM: Homo sapiens

<400> SEQUENCE: 202
cgggctgaag tcggggtgct cggccagcgt cgccgcctgc cggggaggct g            51

<210> SEQ ID NO 203
<211> LENGTH: 51
<212> TYPE: DNA
<213> ORGANISM: Homo sapiens

<400> SEQUENCE: 203
ggtggccatc accgtgccca gcgcctggcc cgcccggccc gacccacgga a            51

<210> SEQ ID NO 204
<211> LENGTH: 51
<212> TYPE: DNA
<213> ORGANISM: Homo sapiens

<400> SEQUENCE: 204
gctgcgcccc gcttgcccctt aaagcagagg tgggatcggg tctcacctct g           51

```
<210> SEQ ID NO 205
<211> LENGTH: 51
<212> TYPE: DNA
<213> ORGANISM: Homo sapiens

<400> SEQUENCE: 205
tcttggtgtt tttttttttaa gttttcccac gagcaaggca gcgaaaatag a          51

<210> SEQ ID NO 206
<211> LENGTH: 51
<212> TYPE: DNA
<213> ORGANISM: Homo sapiens

<400> SEQUENCE: 206
ctgctgctgg gctggtgtcc cttcgagggc tccgcgcgcc tggagccctc a          51

<210> SEQ ID NO 207
<211> LENGTH: 51
<212> TYPE: DNA
<213> ORGANISM: Homo sapiens

<400> SEQUENCE: 207
actgcacgcg ctgacgcgcc tcgcgctcga aggccgcctt gtcctccagg a          51

<210> SEQ ID NO 208
<211> LENGTH: 51
<212> TYPE: DNA
<213> ORGANISM: Homo sapiens

<400> SEQUENCE: 208
gcggcgccag gaacagtagc tgctcgtact tggcgcgaat ccacgactcg c          51

<210> SEQ ID NO 209
<211> LENGTH: 51
<212> TYPE: DNA
<213> ORGANISM: Homo sapiens

<400> SEQUENCE: 209
gctctcgtga tgtccgacgg cactcaccat ttctaggctt ccaggaggtc c          51

<210> SEQ ID NO 210
<211> LENGTH: 51
<212> TYPE: DNA
<213> ORGANISM: Homo sapiens

<400> SEQUENCE: 210
cgcacttgac gcgtccgggc gcctccgcgg tgagtcgcgc cgccgctctc g          51

<210> SEQ ID NO 211
<211> LENGTH: 51
<212> TYPE: DNA
<213> ORGANISM: Homo sapiens

<400> SEQUENCE: 211
atgcctcgcc aggccacgtc gcggttggtg gtcggagagg gcgagggtc c           51

<210> SEQ ID NO 212
<211> LENGTH: 51
<212> TYPE: DNA
<213> ORGANISM: Homo sapiens

<400> SEQUENCE: 212
gggcgggcgc cgctgagcgc gtctaggtgg ccgcaggtcg cggcatcgcg t          51
```

<210> SEQ ID NO 213
<211> LENGTH: 51
<212> TYPE: DNA
<213> ORGANISM: Homo sapiens

<400> SEQUENCE: 213
cccggcacgc acgagaggtg gcgcggctcc ttctcgccga cgccgcggaa a            51

<210> SEQ ID NO 214
<211> LENGTH: 51
<212> TYPE: DNA
<213> ORGANISM: Homo sapiens

<400> SEQUENCE: 214
gtgactttta tgcgggcgcc ccgcggccag gcgtgtgtgc tccgaccggc t            51

<210> SEQ ID NO 215
<211> LENGTH: 51
<212> TYPE: DNA
<213> ORGANISM: Homo sapiens

<400> SEQUENCE: 215
aggaagcccg ggtccaacac cagctgctgg agccgcctca gccgcacctc g            51

<210> SEQ ID NO 216
<211> LENGTH: 51
<212> TYPE: DNA
<213> ORGANISM: Homo sapiens

<400> SEQUENCE: 216
gaggccgagg cgggcggatc acctgaggtt aggagttcaa gaccagcgtg g            51

<210> SEQ ID NO 217
<211> LENGTH: 51
<212> TYPE: DNA
<213> ORGANISM: Homo sapiens

<400> SEQUENCE: 217
cgctgccgtt gacgtcgaag aacttggcgt agtgcagcgg cgacgcggcg t            51

<210> SEQ ID NO 218
<211> LENGTH: 51
<212> TYPE: DNA
<213> ORGANISM: Homo sapiens

<400> SEQUENCE: 218
tcatggggta gcgtatggcg cgcagcgccc gctcggccac ggcaggggc g             51

<210> SEQ ID NO 219
<211> LENGTH: 51
<212> TYPE: DNA
<213> ORGANISM: Homo sapiens

<400> SEQUENCE: 219
gccgagcgcg ccgcgcaggc gcacggcccg gccgccgccg ccgtcgccgc c            51